US011534426B1

(12) United States Patent
Evans et al.

(10) Patent No.: US 11,534,426 B1
(45) Date of Patent: Dec. 27, 2022

(54) USE OF ERGOTHIONEINE FOR EXTENDING LIFESPAN OR IMPROVING HEALTHSPAN

(71) Applicant: Nanjing Nutrabuilding Bio-tech Co., Ltd., Nanjing (CN)

(72) Inventors: Joseph L. Evans, Saint Louis, MO (US); Qiru Fan, Nanjing (CN); Shawn Wells, Lewisville, TX (US); Kylin Liao, Nanjing (CN)

(73) Assignee: Nanjing Nutrabuilding Bio-tech Co., Ltd., Nanjing (CN)

( * ) Notice: Subject to any disclaimer, the term of this patent is extended or adjusted under 35 U.S.C. 154(b) by 0 days.

(21) Appl. No.: 17/585,455

(22) Filed: Jan. 26, 2022

(51) Int. Cl.
C07D 233/84 (2006.01)
A61K 31/417 (2006.01)
A61P 39/06 (2006.01)

(52) U.S. Cl.
CPC ............ *A61K 31/417* (2013.01); *A61P 39/06* (2018.01)

(58) Field of Classification Search
CPC ...... C07D 233/84; A61K 31/417; A61P 39/06
See application file for complete search history.

(56) References Cited

PUBLICATIONS

Gruber et al., Mitochondria-Targeted Antioxidants and Metabolic Modulators as Pharmacological Interventions to Slow Ageing, Biotechnology Advances, vol. 31, No. 5, pp. 563-592 (Year: 2013).*

C. Murphy, et al., 2003. "Genes That Act Downstream of DAF-16 to Influence the Lifespan of Caenorhabditis Elegans." Nature 424 (6946): 277-83.
F. Amrit, et al., The C. elegans lifespan assay toolkit. Methods 68, 465-475 (2014).
I. Cheah, et al., "Ergothioneine; antioxidant potential, physiological function and role in disease," Biochimica et Biophysica Acta (BBA)—Molecular Basis of Disease. 2012, 1822 (5): 784-93.
I. Cheah, et al., Inhibition of Amyloid-Induced Toxicity by Ergothioneine in a Transgenic Caenorhabditis Elegans Model, FEBS Letters 2019, 593 (16): 2139-50.
J. Gruber, et al., 2009. "Deceptively Simple but Simply Deceptive-Caenorhabditis Elegans Lifespan Studies: Considerations for Aging and Antioxidant Effects." FEBS Lett. 583 (21): 3377-87.
K. Pallau, et al., Resveratrol and Lifespan in Model Organisms, Curr. Med. Chem., 2016;23(41):4639-4680.
M. Hansen, et al., 2018. "Autophagy as a Promoter of Longevity: Insights from Model Organisms." Nature Reviews. Molecular Cell Biology 19 (9): 579-93.
N. Stroustrup, et al., The Caenorhabditis elegans Lifespan Machine. Nat Methods 10, 665-670 (2013).
S. Han, et al., OASIS 2: online application for survival analysis 2 with features for the analysis of maximal lifespan and healthspan in aging research. Oncotarget. 7:56147-56152. (2016)).
T. Liu, et al., Resveratrol Attenuates Oxidative Stress and Extends Life Span in the Annual Fish Nothobranchius guentheri, Rejuvenation Res., 2015;18(3):225-33).

* cited by examiner

*Primary Examiner* — Brenda L Coleman
(74) *Attorney, Agent, or Firm* — Weisun Rao; Sunyong Tang; Venture Partner, LLC

(57) ABSTRACT

Among others, the present invention provides novel methods for extending lifespan or improving healthspan in a mammal, which include administration to the mammal of a composition containing a therapeutically effective amount of ergothioneine, or a pharmaceutically acceptable salt, acid, ester, analog or derivative thereof.

9 Claims, 11 Drawing Sheets

USE OF ERGOTHIONEINE FOR EXTENDING LIFESPAN OR IMPROVING HEALTHSPAN

BACKGROUND OF THE INVENTION

Ergothioneine ("Ergo") is a naturally occurring amino acid and is a thiourea derivative of histidine, containing a sulfur atom on the imidazole ring. This compound occurs in relatively few organisms, notably Actinobacteria, Cyanobacteria, and certain fungi. In humans, ergothioneine is acquired exclusively through the diet and accumulates in erythrocytes, bone marrow, liver, kidney, seminal fluid, and eyes.

Resveratrol is a stilbenoid, a type of natural phenol. Sources of resveratrol in food include the skin of grapes, blueberries, raspberries, mulberries, and peanuts. Resveratrol is thought to act like antioxidants, protecting the body against damage that can put you at higher risk for things like cancer and heart disease. There is extensive evidence in experimental models (e.g., yeast, fruit flies, fish, and rodents) that resveratrol extends lifespan (K. Pallau et al., Curr. Med. Chem., 2016; 23(41):4639-4680; T. Liu et al., Rejuvenation Res., 2015; 18(3):225-33). In addition, there is evidence that resveratrol improves risk factors for chronic diseases that are consistent with increased lifespan in humans.

*C. elegans* is a transparent worm about 1 mm in length that lives in temperate soil environments. It has been extensively used as a model organism because it has all the physiological properties of an animal, the ability to replicate human diseases, and a fast life cycle. A model organism is a non-human species that is extensively studied to understand particular biological phenomena, with the expectation that discoveries made in the model organism will provide insight into the workings of other organisms. Model organisms are widely used to research human disease when human experimentation would be unfeasible or unethical. This strategy is made possible by the common descent of all living organisms, and the conservation of metabolic and developmental pathways and genetic material over the course of evolution.

In vitro, ergothioneine requires a specific transporter, ETT, also known as OCTN1 (gene symbol SLC22A4), to enter cells. Although the effect of ergothioneine in vivo is an active area of research, its physiological role in humans is undetermined (Cheah I K, Halliwell B, Biochimica et Biophysica Acta (BBA)—Molecular Basis of Disease. 2012, 1822 (5): 784-93).

SUMMARY OF THE INVENTION

In a first aspect, the present invention provides a method for extending lifespan or improving healthspan of a mammal. The method includes administration to the mammal of a composition comprising therapeutically effective amount of ergothioneine, or a pharmaceutically acceptable salt, acid, ester, analog or derivative thereof.

In some embodiments, the mammal is a human, horse, cattle or other ruminants, pig, or a pet.

In some embodiments, the composition is prepared in a form of food, drink, nutritional composition, or pharmaceutical composition.

In some embodiments, the composition is in a form of solution, liquid suspension, parenteral solution, injectable solution, tablet, pill, granule, powder, film, (micro)capsule, aerosol, tonic, syrup, beverage, or dietary supplement.

In some embodiments, the administration is at least once a day or more times a day.

In some embodiments, the administration is through various routes selected from oral, intravenous injectable, intramuscular injectable, intraperitoneal, intranasal, rectal, or sublingual route.

In some embodiments, the administration of the composition is by oral with a daily dose of ergothioneine in the range of 2-2000 mg, 2-500 mg, 2-200 mg, 2-150 mg, 5-100 mg, or 5-50 mg.

In some embodiments, the daily dose is administered in divided doses or a single dose.

In some embodiments, ergothioneine is a salt, acid, or derivative.

In some embodiments, the composition extending lifespan or improving healthspan is through regulation of insulin signaling, autophagy, reactive oxygen species, and/or protein translation.

In some embodiments, regulation of insulin signaling comprises downregulating expression of one or more genes including dsf-2, dsf-16, daf-18, rsks-1, mtl-1, sod-2, and Nrf2.

In some embodiments, regulation of autophagy comprises downregulating cpr-1 gene expression.

In some embodiments, regulation of reactive oxygen species comprises downregulating sod-2 gene expression.

In some embodiments, regulation of protein translation comprises downregulating ife-2 gene expression.

In a second aspect, the present invention provides a composition comprising therapeutically effective amount of ergothioneine, for extending lifespan or improving healthspan in a mammal.

In some embodiments, the mammal is a human, horse, cattle or other ruminants, pig, or a pet.

In some embodiments, the composition is in a form of food, drink, nutritional composition, or pharmaceutical composition.

In some embodiments, the composition is in a form of solution, liquid suspension, parenteral solution, injectable solution, tablet, pill, granule, powder, film, (micro)capsule, aerosol, tonic, syrup, beverage, or dietary supplement.

In some embodiments, ergothioneine is a salt, acid, or derivative.

In a third aspect, the present invention provides use of the composition disclosed herein, for extending lifespan or improving healthspan in a mammal.

In some embodiments, ergothioneine is administrated at a daily dose of 2-2000 mg, 2-500 mg, 2-200 mg, 2-150 mg, 5-100 mg, or 5-50 mg.

In some embodiments, the daily dose is administered in divided doses or a single dose.

In some embodiments, the administration is at least once a day or more times a day.

In some embodiments, the administration is through various routes selected from oral, intravenous injectable, intramuscular injectable, intraperitoneal, intranasal, rectal, or sublingual route.

In some embodiments, composition disclosed herein extending lifespan or improving healthspan is through regulation of insulin signaling, autophagy, reactive oxygen species, and/or protein translation.

In some embodiments, regulation of insulin signaling comprises downregulating expression of one or more genes including dsf-2, dsf-16, daf-18, rsks-1, mtl-1, sod-2, and Nrf2.

In some embodiments, regulation of autophagy comprises downregulating cpr-1 gene expression.

In some embodiments, regulation of reactive oxygen species comprises downregulating sod-2 gene expression.

In some embodiments, regulation of protein translation comprises downregulating ife-2 gene expression.

In a fourth aspect, the present invention provides a method for preparing a composition disclosed herein.

These and other features, aspects, and advantages of the present invention will become better understood with reference to the following description and appended claims.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5A is the Spatial Distribution, where "(1-normalized mutual information)" measures changes in the spatial distribution of active worms between time points. FIG. 5B is the Centroid Distance, where the "normalized minimum centroid distance" measures the changes in the location of active worms as a group between time points.

FIG. 6A shows the average length of worms, which was measured along a central spline fitted to the worm outline.

FIG. 6B shows the average width of worms, which was measured at the widest point orthogonal to the central spline. FIG. 6C shows the average area of worms, which is the total pixel area of the worm outline converted to $\mu m^2$.

FIG. 9A, Ergothioneine Day 3 vs. Control Day 3. FIG. 9B, Ergothioneine Day 10 vs. Control Day 10. FIG. 9C, Ergothioneine Day 10 vs. Ergothioneine Day 3. FIG. 9D, Control Day 10 vs. Control Day 3.

DETAILED DESCRIPTION OF THE INVENTION

Figure 1:
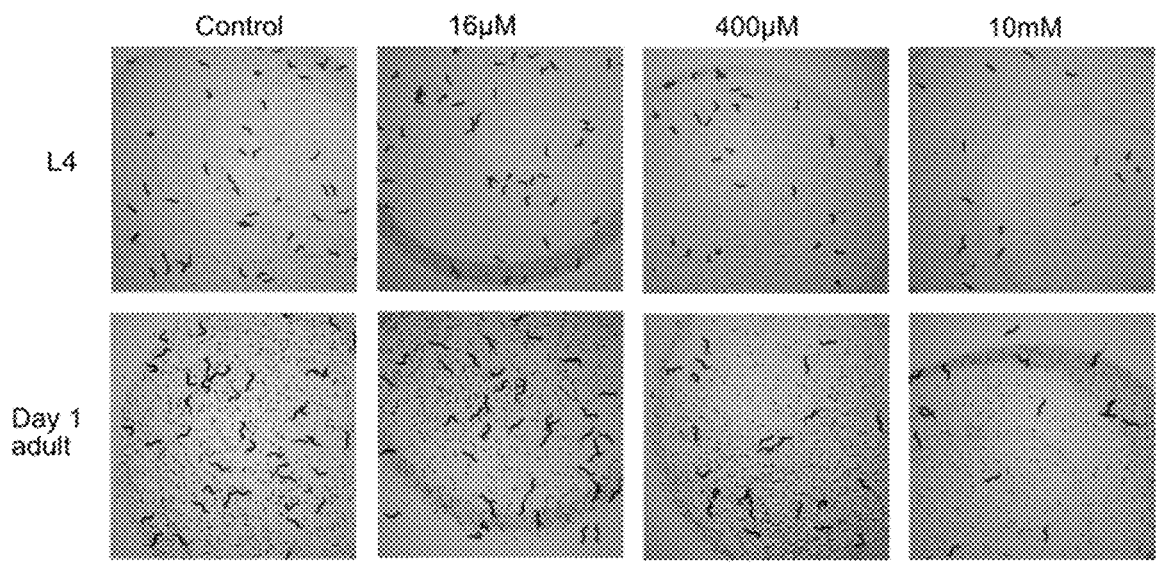
FIG. 1 shows the results of growth and toxicity assays. Each panel is one representative image from three replicates used for measuring worm size and growth with ergothioneine exposure.

In the Summary Section above and the Detailed Description Section, and the claims below, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

In a first aspect, the present invention provides a method for extending lifespan or improving healthspan in a mammal. The method includes administration to the mammal of a composition comprising therapeutically effective amount of ergothioneine, or a pharmaceutically acceptable salt, acid, ester, analog or derivative thereof.

In a second aspect, the present invention provides a composition comprising therapeutically effective amount of ergothioneine, for extending lifespan or improving healthspan in a mammal.

In a third aspect, the present invention provides use of the composition disclosed herein, for extending lifespan or improving healthspan in a mammal.

In a fourth aspect, the present invention provides a method for preparing a composition disclosed herein.

As used herein, "lifespan" refers to the length of time for which a mammal lives. "Extending lifespan" refers to the increase of the length of time for which a mammal lives. An example of lifespan extending can be seen at Example 2 below.

As used herein, "healthspan" refers to the length of time for which a mammal is generally in good health. Certain features of a mammal can be used as a proxy for its health. For example, moving activity and morphology can serve as a proxy for C. elegans' health. See Example 3 below. "Improving healthspan" refers to the increase of the length of time for which a mammal is generally in good health.

Ergothioneine is a naturally occurring amino acid and is a thiourea derivative of histidine, containing a sulfur atom on the imidazole ring. This compound occurs in relatively few organisms, notably Actinobacteria, Cyanobacteria, and certain fungi. In humans, ergothioneine is acquired exclusively through the diet and accumulates in erythrocytes, bone marrow, liver, kidney, seminal fluid, and eyes. In vitro, ergothioneine requires a specific transporter, ETT, also known as OCTN1 (gene symbol SLC22A4), to enter cells. Although the effect of ergothioneine in vivo is an active area of research, its physiological role in humans is undetermined (Cheah I K, Halliwell B, Biochimica et Biophysica Acta (BBA)—Molecular Basis of Disease. 2012, 1822 (5): 784-93).

Serendipitously, the inventors have discovered that Ergothioneine can extend lifespan and improve healthspan of an animal (see Example section below).

As used herein, a "therapeutically effective amount" refers to a sufficient amount of ergothioneine for extending lifespan or improving healthspan in a mammal, at a reasonable benefit/risk ratio applicable to any medical treatment. It will be understood, however, that the total daily usage of ergothioneine may be decided by the attending physician within the scope of sound medical judgment. The specific therapeutically effective dose level for any particular subject will depend upon a variety of factors including the disorder being treated and the severity of the disorder; the specific composition employed, the age, body weight, general health, sex and diet of the subject; the time of administration, route of administration, and rate of excretion of ergothioneine employed; the duration of the treatment; drugs used in combination or coincidental with ergothioneine; and like factors well known in the medical arts. For example, it is well known within the skill of the art to start doses of the compound at levels lower than those required to achieve the desired therapeutic effect and to gradually increase the dosage until the desired effect is achieved. In addition, a "therapeutically effective amount" is the amount that will elicit the biological or medical response of a tissue, system, or subject that is being sought by a researcher or clinician, and in particular elicit some desired therapeutic or prophylactic effect for extending lifespan or improving healthspan in a mammal.

One of skill in the art recognizes that an amount may be considered therapeutically "effective" even if the condition is not totally eradicated or prevented, but it or its symptoms and/or effects are improved or alleviated partially in the subject. Various indicators for determining the effectiveness of a method for extending lifespan or improving healthspan in a mammal are known to those skilled in the art.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

In some embodiments, the composition comprises from about 5% to about 10%, 20%, 30%, 40%, 50%, 60%, 70%, 80%, 90%, or 95% by weight of ergothioneine, and preferably from about 30% to about 90% by weight of ergothioneine, based upon the total weight of the composition taken as 100% by weight.

Other ingredients may be included in the claimed composition, such as other active agents, preservatives, buffering agents, salts, a pharmaceutically acceptable carrier, or other pharmaceutically acceptable ingredients.

As used herein, a "carrier" refers to a compound that facilitates the incorporation of a compound into cells or tissues. For example, without limitation, dimethyl sulfoxide (DMSO), Ethanol (EtOH), or PEG400 is a commonly utilized carrier that facilitates the uptake of many organic compounds into cells or tissues of a subject.

"Mammal" includes, without limitation, mice, rats, rabbits, guinea pigs, dogs, cats, sheep, goats, cattle, horses, primates, such as monkeys, chimpanzees, and apes, and, in particular, humans.

In some embodiments, the mammal is a human, cattle, or a pet. "Pet" includes, without limitation, mice, rats, rabbits, guinea pigs, dogs, cats, fish, reptiles, and sheep.

In some embodiments, the composition is prepared in a form of food, drink, nutritional composition, or pharmaceutical composition.

The term "pharmaceutical composition" refers to a mixture of ergothioneine with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid and salicylic acid. Pharmaceutical compositions will generally be tailored to the specific intended route of administration. A pharmaceutical composition is suitable for human and/or veterinary applications.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes.

The pharmaceutical compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include ergothioneine formulated in a compatible pharmaceutical carrier may also be prepared, placed in an appropriate container, and labeled for treatment of an indicated condition.

In some embodiments, the composition is in a form of solution, liquid suspension, parenteral solution, injectable solution, tablet, pill, granule, powder, film, (micro)capsule, aerosol, tonic, syrup, beverage, or dietary supplement.

As used herein, a "parenteral solution" refers to a solution that can be administered elsewhere in the body than the mouth and alimentary canal. It is not delivered via the intestinal tract. For example, parenteral solution can be delivered intravenously.

As used herein, a "tonic" refers to a medicinal substance taken to give a feeling of vigor or well-being.

As used herein, a "syrup" refers to a thick sticky liquid derived from a sugar-rich plant, for example, sugar cane, corn, and maple.

In some embodiments, the administration is at least once a day or more times a day.

Multiple techniques of administering a composition exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. One may also administer the composition in a local rather than systemic manner, for example, via injection of the compound directly into the infected area, often in a depot or sustained release formulation. Furthermore, one may administer the composition in a targeted drug delivery system, for example, in a liposome coated with a tissue specific antibody. The liposomes will be targeted to and taken up selectively by the organ.

In some embodiments, the administration is through various routes selected from oral, intravenous injectable, intramuscular injectable, intraperitoneal, intranasal, rectal, or sublingual route.

"Intraperitoneal" as used here means within or administered through the peritoneum. The peritoneum is a thin, transparent membrane that lines the walls of the abdominal (peritoneal) cavity and contains/encloses the abdominal organs such as the stomach and intestines.

As used herein, "sublingual" refers to situated or applied under the tongue.

In some embodiments, the administration of the composition is by oral with a daily dose of ergothioneine in the range of 2-2000 mg. In some embodiments, the administration of the composition is by oral with a daily dose of ergothioneine in the range of 5-500 mg. In some embodiments, the administration of the composition is by oral with a daily dose of ergothioneine in the range of 5-25 mg.

The dosage may range broadly, depending upon the desired effects and the therapeutic indication. The daily dosage regimen for an adult human patient may be, for example, an oral dose of between 0.01 mg and 3000 mg of ergothioneine, preferably between 1 mg and 700 mg, e.g. 5 to 200 mg, or between about 0.1 mg and about 1,000 mg of ergothioneine per kg of body weight of the subject. The dosage may be a single one or a series of two or more given in the course of one or more days, as is needed by the subject. In some embodiments, the compounds are administered for a period of continuous therapy, for example for a week or more, or for months or years. In some embodiments, ergothioneine, or a pharmaceutically acceptable salt thereof, can be administered less frequently compared to the frequency of administration of an agent within the standard of care. In some embodiments, ergothioneine, or a pharmaceutically acceptable salt thereof, can be administered one time per day. In some embodiments, the total time of the treatment regime with ergothioneine, or a pharmaceutically acceptable salt thereof, can be less compared to the total time of the treatment regime with the standard of care.

In instances where human dosages for ergothioneine have been established for at least some condition, those same dosages may be used, or dosages that are between about 0.1% and 500%, more preferably between about 25% and 250% of the established human dosage. Where no human dosage is established, as will be the case for newly discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

As used herein, the term "$ED_{50}$" refers to the dose that produces the desired effect in 50% of the population, or median effective dose.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety that are sufficient to maintain the modulating effects, or minimal effective concentration (MEC). Dosages necessary to achieve the MEC will depend on individual characteristics and route of administration. However, HPLC assays or bioassays can be used to determine plasma concentrations. Dosage intervals can also be determined using MEC value. Compositions should be administered using a regimen that maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

In some embodiments, the daily dose is administered in divided doses or a single dose.

In some embodiments, ergothioneine is referred to its corresponding salts, acids, or derivatives.

In some embodiments, the composition comprising therapeutically effective amount of ergothioneine, or a pharmaceutically acceptable salt, acid, ester, analog or derivative thereof extending lifespan or improving healthspan is through regulation of insulin signaling, autophagy, reactive oxygen species, and/or protein translation.

In some embodiments, regulation of insulin signaling comprises downregulating expression of one or more genes including dsf-2, dsf-16, daf-18, rsks-1, mtl-1, sod-2, and Nrf2.

In some embodiments, regulation of autophagy comprises downregulating cpr-1 gene expression.

In some embodiments, regulation of reactive oxygen species comprises downregulating sod-2 gene expression.

In some embodiments, regulation of protein translation comprises downregulating ife-2 gene expression.

Some functions of dsf-2, dsf-16, daf-18, rsks-1, mtl-1, sod-2, Nrf2, cpr-1, and ife-2 are described in Example 5.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' desired/or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least." When used in the context of a process, the term "comprising" means that the process includes at least the recited steps, but may include additional steps. When used in the context of a composition, composition or device, the term "comprising" means that the composition, composition or device includes at least the recited features or components, but may also include additional features or components. Likewise, a group of items linked with the conjunction "and" should not be read as requiring that each and every one of those items be present in the grouping, but rather should be read as 'and/or' unless expressly stated otherwise. Similarly, a group of items linked with the conjunction "or" should not be read as requiring mutual exclusivity among that group, but rather should be read as "and/or" unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

Any titles or subheadings used herein are for organization purposes and should not be used to limit the scope of embodiments disclosed herein.

All publications and patent applications cited in this specification are herein incorporated by reference as if each individual publication or patent application were specifically and individually indicated to be incorporated by reference.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

Materials and Methods
C. elegans Strain Used
N2 (Bristol) wild type strain has been used in this application.
Worm Maintenance and Media
To prevent chemical modification or metabolism of the test article by the food bacteria, worms were fed on a lawn of UV-killed bacteria (UV-i bacteria). An overnight culture of E. coli strain WP-2 was pelleted, washed, filtered, and irradiated. A suspension of UV-i bacteria was spotted on NGM agar containing Streptomycin to inhibit the growth of contaminating bacteria. The quantity and distribution of food bacteria were calibrated to ensure adequate access to food for the duration of assay while maintaining visibility of the worms.
Automated Lifespan Machine (ALM)
The ALM used herein is based on the Caenorhabditis elegans lifespan machine published by Stroustrup et. al (Stroustrup, N. et al. The Caenorhabditis elegans Lifespan Machine. Nat Methods 10, 665-670 (2013)), with proprietary modifications to improve temperature stability and image acquisition. The scanner unit consists of a modified EPSON V850 and images are processed and analyzed using the ALM software (see id.). The machine time-of-death calls are trained and validated using the "storyboarding" feature of the ALM software.
Lifespan Assay
The lifespan assay was designed and performed according to published and validated methods (Amrit, F. R. G., Ratnappan, R., Keith, S. A. & Ghazi, A. The C. elegans lifespan assay toolkit. Methods 68, 465-475 (2014)), using a modified version of the Automated Lifespan Machine (Stroustrup, N. et al. The Caenorhabditis elegans Lifespan Machine. Nat Methods 10, 665-670 (2013)). Worms were age synchronized by bleaching and eggs were plated directly onto NGM agar seeded with UV-i bacteria (Day 1, hatch). On Day 3, when the worms had reached the late L4 stage, they were transferred to dishes containing 100 µM 5-Fluorodeoxyuridine (FUdR) to suppress progeny. On day 5, the worms were washed off the dishes, and 30-50 worms were plated on each scanner dish. Plates were immobilized inverted on the bed of an Automated Lifespan Machine which scanned two images per hour of the plates continuously for the next 40 days.
Survival Analysis
Time of death calls exported from the ALM software was analyzed and plotted using the Lifelines software package developed by Cam Davidson-Pilon et. al (Lifelines Version: v0.25.9). Additional analysis performed using the OASIS2 analysis software (Seong Kyu Han et. al. OASIS 2: online application for survival analysis 2 with features for the analysis of maximal lifespan and healthspan in aging research. Oncotarget. 7:56147-56152. (2016)).
Movement and Healthspan Analysis
Worm movement was tracked from the images acquired by the ALM during the lifespan assay. Worm size and movement features were extracted and analyzed using custom software.
Analysis of Gene Expression by qPCR
Day 1 adult animals were harvested for RNA extraction. Biological replicates were prepared from independently synchronized populations. For RNA extraction, worms were harvested by filtration, washed with M9+0.1% Tween 20 to remove bacteria, pelleted, resuspended in Trizol (TRI-Reagent, Zymo) and then frozen. RNA was extracted using Direct-zol RNA Miniprep Kit (Zymo). Concentration and quality of RNA was measured using a Qubit 6 fluorometer. All samples showed a Qubit IQ score>8.0 indicating that the RNA was intact. Multiplex qPCR reactions were set up with three technical replicates per sample and two endogenous controls (cdc-42 and pmp-3). Reactions were run on a QuantStudio6 (Thermo) and data was analyzed using Thermo Cloud Connect and Prizm 8.0 (GraphPad).

Whole Transcriptome Analysis

More than 150 day-1 adult worms per replicate were harvested, cleaned by filtration, and frozen at −80° C. in Trizol. To extract RNA, samples were thawed, vigorously vortexed, and processed using the Direct-zol RNA Miniprep Kit (Zymo Research). All samples exceeded our threshold for RNA quantity and quality.

RNA samples were submitted to Novogene Co. Ltd and subjected to more stringent QC, being tested on a Qubit for concentration and run on an agarose gel and on the Agilent 2100 to assess RNA quality and integrity. All samples had an RNA Integrity Number (RIN) of 8.8 or higher (range is 0-10, with 10 being "perfect").

The total RNA is then enriched for poly-mRNA using oligo(dT) paramagnetic beads. DNA libraries were then constructed from this input mRNA using the NEB Next Ultra™ II RNA Library Prep Kit. This creates a ready-to-sequence dsDNA library that retains the strand-specific information in the original mRNA. These libraries were then further tested by the Qubit for concentration and the Agilent 2100 for library size distribution and quality. In order to properly pool the libraries and load them onto sequencing lanes to ensure the correct number of reads per sample, an even more precise quantification of the library was done via qPCR, and the samples were loaded onto the NovaSeq 6000 platform for a paired-end sequencing run of 150 bp for each end (PE150). The loading concentrations were designed to obtain at least 6.0 Gb (which is the number of billion bases of raw data, determined by the number of reads multiplied by the length of each read).

Sequencing run data quality control was performed both by Novogene and again by inventors of this application. The raw data set was analyzed for:
1. The distribution of base quality along the length of the sequencing read;
2. The distribution of error rate along the length of the sequencing read;
3. The distribution of A/T/G/C bases along the length of the sequencing read;
4. The distribution of raw data filtering results based on the following three criteria:
   a. Removing reads containing adapter sequence,
   b. Remove reads with N>10% (where N means "base cannot be determined"),
   c. Remove reads with a low quality (Qscore<=5) for 50% or more of its total bases.

Example 1

This example describes the tests of various dosages of ergothioneine and their toxicity on *C. elegans*.

Background

The ideal dose of a lifespan-extending composition will balance providing a high enough dose to be effective with low enough doses not to cause toxic or aversive reactions to the treating animals.

Dosage and Toxicity Tests

*C. elegans* was used in this study because it has advantages including having all the physiological properties of an animal, the ability to replicate human diseases, and a fast life cycle. The body of *C. elegans* is encased in a selectively permeable cuticle that only permits some compounds to be absorbed efficiently through the skin, so the most reliable mechanism for delivering compounds to the worms is through ingestion. Water-soluble compounds permeate the media and food and are readily taken up by the worms.

Making culturing plates with ergothioneine: *C. elegans* is usually grown in the laboratory using *E. coli* as a food source. Nematode Growth Medium (NGM) plates have been prepared by aseptically pouring NGM agar into petri plates. Ergothioneine was dissolved in water to make a working solution of 0.5 M and then mixed with *E. coli* liquid culture before seeding on NGM agar plates. The seeding spots were dried slowly, allowing ergothioneine to diffuse into the food bacteria and the agar for at least 24 hours before worms are introduced. The indicated ergothioneine dosages (0, 640 nM, 3.2 µM, 16 µM, 80 µM, 400 µM, 2 mM, and 10 mM) are based on the total volume of the plates.

Growth and Development Assay Results

High-resolution imaging and automated detection were used to precisely measure the growth rate of *C. elegans* worms from hatching to the first day of adulthood (total of 4 days). The *C. elegans* growth and development assay is highly sensitive and widely used in toxicology studies. Performing this test over a range of doses helps to identify a set of doses that have a physiological impact and exclude dose ranges that are likely too toxic to benefit lifespan.

FIG. 1 shows the results of growth and toxicity assays. Each panel is one representative image from three replicates used for measuring worm size and growth with ergothioneine exposure. Concentrations of ergothioneine are shown above the top row. Images were acquired using WormLab imager and measured using automated detection and measurement. As shown in FIG. 1, 16 µM and 400 µM ergothioneine treatment resulted in comparable number and size of *C. elegans* for L4 and day 1 adult. On the other hand, 10 mM resulted in less worms at both L4 and day 1 adult stages.

Figure 2:
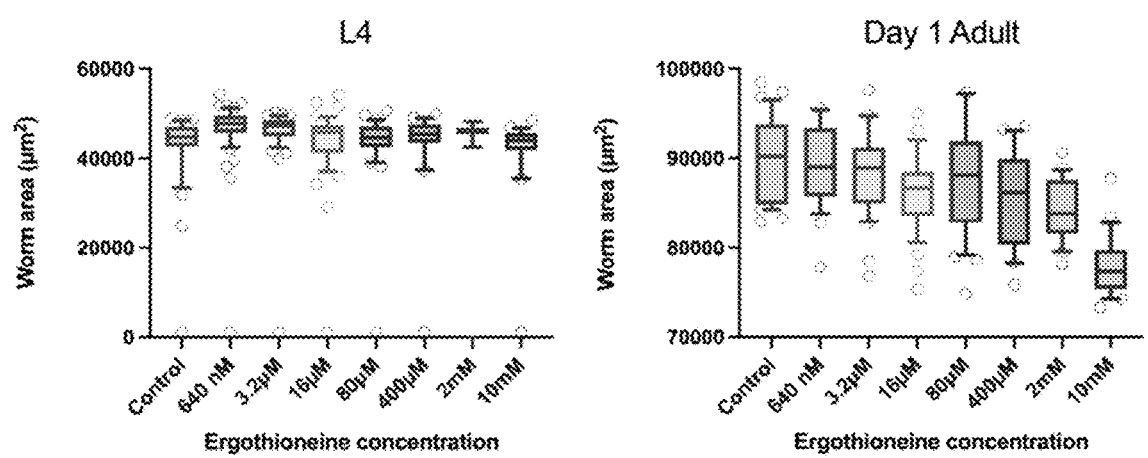
FIG. 2 shows growth and toxicity assay plots of worm size data obtained from high resolution imaging and automated detection and tracking software. Left panel shows the results of worms at L4 stage; right panel shows the results of worms at Day 1 adult stage.

FIG. 2 shows growth and toxicity assay plots of worm size data obtained from high resolution imaging and automated detection and tracking software. Line=mean area, box=25th to 75th percentile, whiskers=10th to 90th percentile. Circles indicate individuals outside the 10th-90th percentile. As can be seen, the growth rate was largely unaffected at concentrations up to 10 mM at L4 stage (left panel). However, at day 1 adult stage, the growth rate was largely unaffected at concentrations up to 2 mM, and at the 10 mM concentration, the young adults were smaller than normal (right panel).

Acute Toxicity Assay Results

The acute toxicity assay tests toxicity in adult worms by simulating the actual conditions of the lifespan assay. This accomplishes two things. First, in the early stages, it determines doses that are acutely toxic to adult worms. Second, over time worm deaths are scored to rule out doses that will likely have a negative impact on lifespan despite lacking immediate toxicity. Worms are plated on the exact media and sealed plates that will be used in the lifespan assay and then incubated at 25° C. to provide a pilot lifespan that helps catch any other dosing and delivery pitfalls early on. Adult worms were monitored in the days immediately following exposure for early lethality or any other obvious defects.

Figure 3:
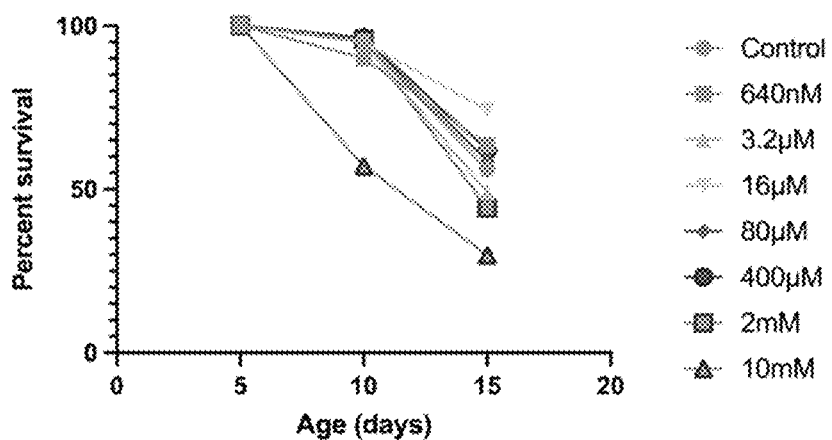
FIG. 3 shows the results of acute toxicity assay where L4 stage C. elegans worms were treated with ergothioneine at concentrations from 640 nM to 10 mM.

Worms were treated with either vehicle control or ergothioneine at doses spanning a range from 650 nM to 10 mM on media identical to what would be used in the lifespan experiment. FIG. 3 shows the results of acute toxicity assay. Large L4 stage worms were plated on solid media identical to that of the actual lifespan assay. Worms were examined for immediate toxic effects and then scored intermittently for survival until the start of lifespan experiment in the next step (see example 2 below). Of all the conditions, as shown in FIG. 3, only the 10 mM dose showed an early lethality at day 10 post treatment, and 2 mM was on the upper end of the remaining doses that did not cause early lethality. This indicated that the dose range of ergothioneine for the lifespan experiment can be at least up to 2 mM. 5 mM ergothioneine has been used before for lifespan extending experiment (Cheah, Irwin K., et. al., Inhibition of Amyloid-Induced Toxicity by Ergothioneine in a Transgenic Caenorhabditis Elegans Model, FEBS Letters 2019, 593 (16): 2139-50). For comparison with this previous study a maximum dose of 5 mM was tested along with two lower concentrations of 0.5 mM and 0.1 mM in the following examples.

Example 2

This example describes assessment and measurement of how ergothioneine mitigates lifespan and healthspan decline.

The lifespan assay was initiated by expanding all replicate groups to more than 1000 worms, then synchronizing by bleaching and allowing larval worms to hatch and arrest. To eliminate the effect of bacterial metabolism and growth on lifespan of C. elegans worms, synchronized worms were only exposed to dead food bacteria. To suppress progeny, worms were transferred to media containing 5-Fluorodeoxyuridine (FUdR) within 54-60 hours post-plating. Worms were inspected 24 and 48 hours after this transfer to confirm infertility. Finally, the worms were inspected for general health and morphology before transferring to scanner plates. The scanner plates were incubated for an additional 2 days and inspected again before loading onto scanners.

To understand the physiological impact of either genetic variation or pharmacological treatment on aging, it is crucial to use quantitative models. The analysis of lifespan data is grounded in the study of two mathematical functions: the survival curve and the hazard function. The survival curve describes the fraction of a tested population that remains alive over time. The hazard function is related to the survival curve and provides an intuitive measure of the risk of death; this function describes the probability that a typical individual who is currently alive will soon die, providing a clear visualization of the way a treatment may change patterns in mortality.

To obtain high-resolution lifespan data and eliminate confounding factors such as worm handling and operator bias, lifespan data was collected using an Automated Lifespan Machine (ALM) (Stroustrup, N. et al. The Caenorhabditis elegans Lifespan Machine. Nat Methods 10, 665-670 (2013)). Three biological replicates, derived from synchronizing three independently maintained lines of N2 worms, were distributed across instruments. Images of the worms were then collected for the next 35 days with no interruption or manipulations. Some plates were excluded after quality checks, but plate number and worm count for all replicates exceeded the threshold for statistical significance (Table 1, row 1).

TABLE 1

Lifespan assay summary of Ergo (ergothioneine) and resveratrol. Lifespan is counted with day 0 set at day 1 of adulthood. No death times are recorded until worms are placed on the scanner on day 8 so earlier deaths are excluded from calculations of mean and median. Median lifespan is equal to the time at which 50% of the worms have died. Mean lifespan is calculated from the area under the survival curve. Maximum lifespan is equal to 95th percentile of lifespans in each group. C.I.: Confidence Interval. See FIGS. 4A-4B and Table 1 for statistical analysis.

|  | Vehicle control | Ergo 0.1 mM | Ergo 0.5 mM | Ergo 5.0 mM | Resveratrol 0.1 mM |
|---|---|---|---|---|---|
| Number of worms | 253 | 226 | 209 | 193 | 184 |
| Median lifespan (days) | 23.6 | 24.2 | 24.2 | 25.9 | 27.3 |
| Median 95% C.I. | 22.0-24.6 | 23.3-25.2 | 22.6-25.2 | 24.8-27.6 | 25.8-28.8 |
| Mean lifespan (days) | 22.9 | 23.4 | 23.5 | 25.3 | 26.3 |
| Mean 95% C.I. | 22.2-23.7 | 22.6-24.2 | 22.7-24.4 | 24.5-26.2 | 25.3-27.4 |
| Maximum lifespan (days) | 32.4 | 33.2 | 33.3 | 34.6 | 37.3 |

Figure 4A:
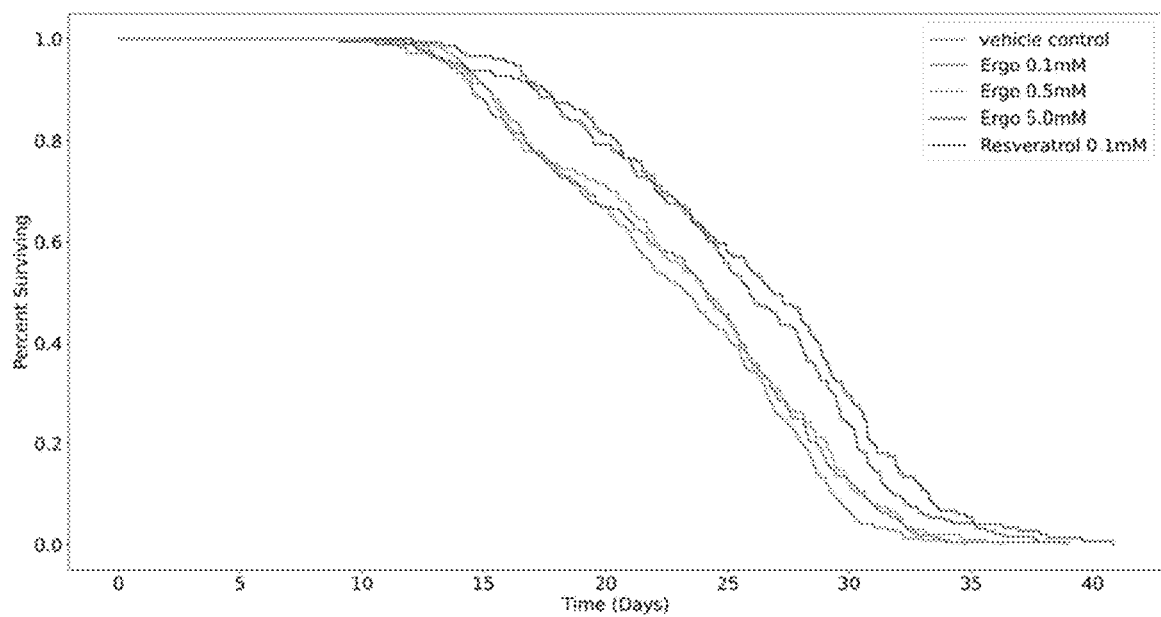
FIG. 4A shows the Kaplan-Meier estimate of the survival function.
Figure 4B:
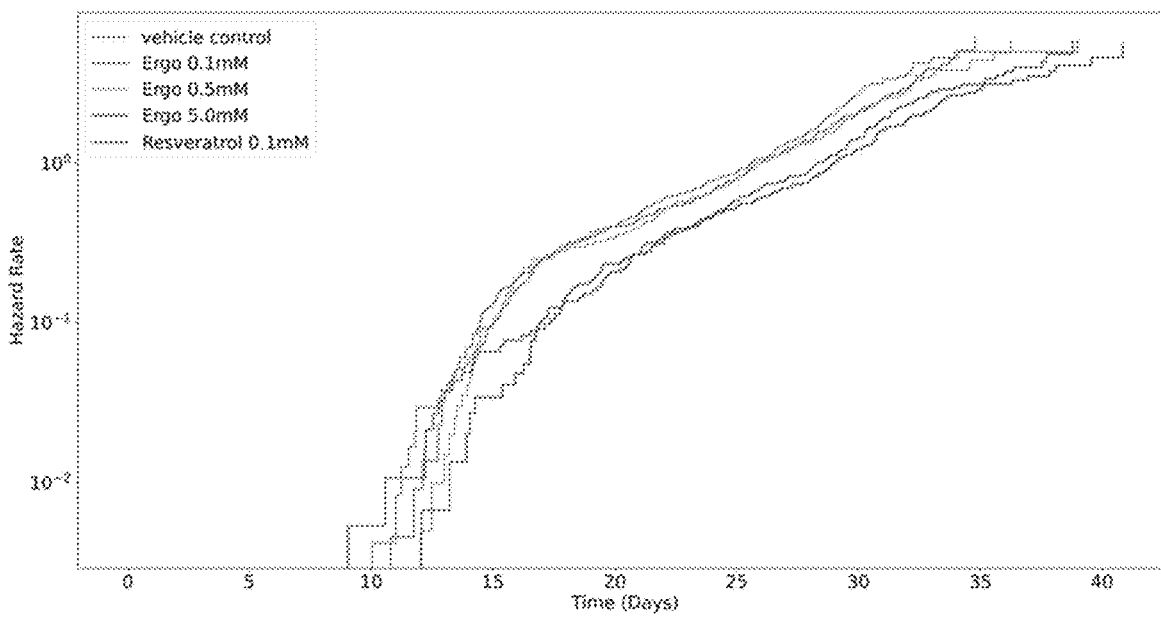
FIG. 4B shows the Nelson-Aalen estimate of hazard rates from lifespan assay.

Lifespan data are represented as the percent of worms surviving over time and the profile of this curve can be modeled by the Kaplan-Meier Estimate of Survival function (FIGS. 4A-4B). FIG. 4A is the Kaplan-Meier estimate of the survival function; FIG. 4B is the Nelson-Aalen estimate of hazard rates from lifespan assay. The survival curves can be compared by several statistics including mean, median, and maximum lifespan (see Table 1), as well as the age of worms at a specific percent survival (see Table 2).

TABLE 2

Age in days at percent mortality. Age at percent mortality is the age in days at which the given percentage of worms are dead. Age at 50% mortality is equal to the median. These analyses are useful for examining early or late life-specific effects or when the survival curves are not parallel. Fisher's Exact Tests for differences at 25, 50, 75, and 90% mortality are shown in Table 4 below.

| treatment | 25% mortality | 50% | 75% | 90% | 100% |
|---|---|---|---|---|---|
| Vehicle control | 17.77 | 23.59 | 27.5 | 29.68 | 38.18 |
| Ergo 0.1 mM | 17.97 | 24.16 | 28.15 | 30.83 | 39 |
| Ergo 0.5 mM | 18.05 | 24.22 | 28.37 | 30.84 | 37.26 |
| Ergo 5.0 mM | 21.04 | 25.92 | 29.73 | 32.05 | 38.81 |
| Resveratrol 0.1 mM | 21.46 | 27.29 | 31.13 | 35.89 | 40.85 |

However, to determine whether one treatment group lived longer than another, survival curves are holistically compared using a log-rank test (see Table 3).

TABLE 3

Pairwise statistical analysis of survival curves. The Mantel-Cox log-rank test is a non-parametric test that compares two survival functions across the duration of the lifespan. The Wilcoxon-Breslow-Gehan test weights each death time by the total number of subjects at risk, thus assigning more weight to earlier death times. P-value is corrected for multiple comparisons (Bonferroni correction). Numbers and asterisks represent P-value and significance, respectively.

| Curve comparison | Mantel-Cox Log Rank | | Wilcoxon-Breslow-Gehan | |
| --- | --- | --- | --- | --- |
| | Test statistic ()(2) | Log-rank test P-value | Test statistic (X2) | Log-rank test P-value |
| Ergo 0.1 mM v.s. vehicle control | 1.22 | 1 | 0.62 | 1 |
| Ergo 0.5 mM vs. vehicle control | 1.40 | 0.95 | 1.02 | 1 |
| Ergo 5.0 mM v.s. vehicle control | 18 | 0.0001  *** | 18.65 | 0.0001  *** |
| Ergo 5.0 mM v.s. Resveratrol 0.1 mM | 8.01 | 0.019 | 2.98 | 0.33 |
| Resveratrol 0.1 mM v.s. vehicle control | 41.57 | <0.00001**** | 30.47 | <0.00001**** |

In this study, all pairwise comparisons between conditions were statistically significant. Tables 1-3 detail the raw measurements, calculations, and statistical analysis related to the survival curve in FIGS. 4A-4B.

Lifespan Results

Overall, the lifespan assay detected a significant positive increase in lifespan in the highest Ergothioneine treatment group as well as the Resveratrol positive control. A minimum of 184 and a maximum of 253 worm lifespans per condition was recorded (Table 1) surpassing the requirement of 150 required to eliminate subsampling errors and detect lifespan differences of 10% or more (Gruber, Jan, Li Fang Ng, Suresh Kumar Poovathingal, and Barry Halliwell. 2009. "Deceptively Simple but Simply Deceptive—*Caenorhabditis Elegans* Lifespan Studies: Considerations for Aging and Antioxidant Effects." FEBS Letters 583 (21): 3377-87). A Cox Proportional Hazards analysis was run to determine if factors other than the treatment could confound the data and no factors other than the incubator were detected. Qualitatively, the worms appeared morphologically and behaviorally normal suggesting that they were not impacted by confounding hazards such as contamination or toxicity.

Worms were treated with three different doses of Ergothioneine-0.1 mM, 0.5 mM and 5.0 mM—as well as a positive control of 0.1 mM Resveratrol. FIG. 4A is the Kaplan-Meier estimate of the survival function, which shows that treatment of worms with Ergothioneine produced a dose-dependent increase in lifespan, with the highest dose having a significant effect comparable to Resveratrol (FIG. 4A). Under ideal conditions, factors that act upon the rate of aging typically produce a survival curve that remains parallel to the control but right- or left-shifted. This is known as "temporal scaling" of lifespan. The Ergothioneine and Resveratrol treatments follow this paradigm running mostly parallel but right-shifted relative to the control group. The hazard rate function is the instantaneous risk of death at a given time and can help indicate whether different survival curves are determined by similar or different risk factors. FIG. 4B is the Nelson-Aalen estimate of hazard rates from lifespan assay. In this case, the roughly parallel hazard rate functions indicate that all treatment groups are responding to similar aging hazards, albeit aging at different rates (FIG. 4B).

Survival curves can be compared descriptively with statistics such as mean, median, and maximum lifespan (Table 1). Treatment with 5.0 mM Ergotheionine increased each of these statistics as did Resveratrol. Whereas the vehicle-treated control group had a median lifespan of 23.6 days, the Ergothioneine and Resveratrol treated groups had median survival of 25.9 and 27.3 days, respectively (see Table 1). By convention, the "maximum lifespan" is typically the 95th percentile of lifespans recorded. Treatment with 5.0 mM Ergothioneine increased the maximum lifespan from the control of 32.4 days to 34.6 days; the Resveratrol group had a maximum lifespan of 37.3 days (see Table 1).

Survival curves also are commonly compared statistically using a log-rank test, which tests the hypothesis that the two curves are sampled from the same population. Treatment with 5.0 mM Ergothioneine produced a statistically significant shift in survival when the curves were analyzed using two contrasting log-rank tests. A standard Mantel-Cox log-rank test compares the curves globally over the course of the lifespan assigning equal weight to each timepoint, whereas the Wilcoxon-Breslow-Gehan weights each death by the number of subjects at risk, assigning greater weight to earlier deaths. Pairwise statistical analysis of survival curves is summarized in Table 3. Each of these tests indicated highly significant differences between 5.0 mM Ergothioneine treatment and controls (Table 3). These same tests indicated that 5.0 mM Ergothioneine treatment increases lifespan similarly to, but slightly less than the Resveratrol positive control.

Ergothioneine and Resveratrol treatments increased lifespan while maintaining the overall shape of the survival curve. Additional analyses are useful when the curves have a more complex shape or cross. Table 2 shows the age in days for multiple levels of mortality. A Fisher's exact test can be also applied to specific time or mortality points of interest.

TABLE 4

Fisher's Exact Test for survival differences at key time points. Statistical analysis corresponding to the age at specific percent mortality shown in Table 2. Age at 50% mortality is equal to the median. These analyses are useful for examining early or late life-specific effects or when the survival curves are not parallel.

| treatment | P-value at 25% mortality | P-value at 50% | P-value at 75% | P-value at 90% |
| --- | --- | --- | --- | --- |
| Ergo 0.1 mM v.s. vehicle control | 0.7523 | 0.2726 | 0.5967 | 0.0204 |
| Ergo 0.5 mM v.s. vehicle control | 0.8294 | 0.4002 | 0.3307 | 0.1194 |
| Ergo 5.0 mM v.s. vehicle control | 0.0014 | 0.0098 | 0.000014 | 0.0006 |
| Ergo 5.0 mM v.s. Resveratrol 0.1 mM | 0.6354 | 0.3035 | 0.0043 | 0.0233 |
| Resveratrol 0.1 mM vs. vehicle control | 0.0012 | 0.0005 | 4.10E−10 | 4.40E−08 |

As shown in Table 4, comparisons between 5 mM Ergo (row 3) and Vehicle were statistically significant at each timepoint, as were the comparisons between 0.1 mM Resveratrol (row 5) and vehicle control. The data demonstrate that the two treatments (5 mM Ergo and 0.1 mM Resveratrol) that increased lifespan showed higher survival than the vehicle control at all timepoints with statistical significance.

Example 3

This example describes healthspan, movement, and morphology of Ergothioneine-treated *C. elegans* worms.

To measure healthspan, active worms were identified using the ALM scanner images from the lifespan assay (see Example 2). The worms' spatial location on the plate and their morphology were quantified throughout their lifespan to assess healthspan.

Worm Activity serves as a proxy for animal health. Changes in spatial distribution of the worms between time points is used to derive aggregate movement for the population over time. Worm Activity is described by two complementary measurements of aggregate movement, Centroid Distance and Spatial Distribution:

Centroid Distance calculates a geometric center for each individual worm, and then measures the minimum collective distance that a group of worms moved between time points. It achieves measurement of the changes in spatial distribution between time-points.

Spatial Distribution uses changes in worm contours between time points to measure the changes in the spatial distribution of the worms' bodies. The normalized distribution of these distances in the population provides a measure of how much the group of worms altered their positions and posture on the plate between two time-points.

For both of these Activity metrics, a plot with higher numbers indicates good health, and all measures are normalized to fall between 0 and 1.

Worm morphology is measured from the worm contours detected in the images. In the process of aging, worms become shorter and stouter over time and their shape is an indicator of their overall health and biological age. The Length is calculated from the central spline fitted to the worm contour and Width is measured from each worm's widest point. The worms' posture also changes with age as they lose the ability to maintain an elongated position. Average Circularity measures how close the shape and posture come to being enclosed by a circle.

Each of these measures are obtained by averaging data for all active worms detected on a plate, then averaging across different replicate plates of the same condition. All measurements are based on worms that are still alive and moving at the time of quantification. All measures start when worms are placed on the scanner at day 3 of adulthood.

Figure 5A:
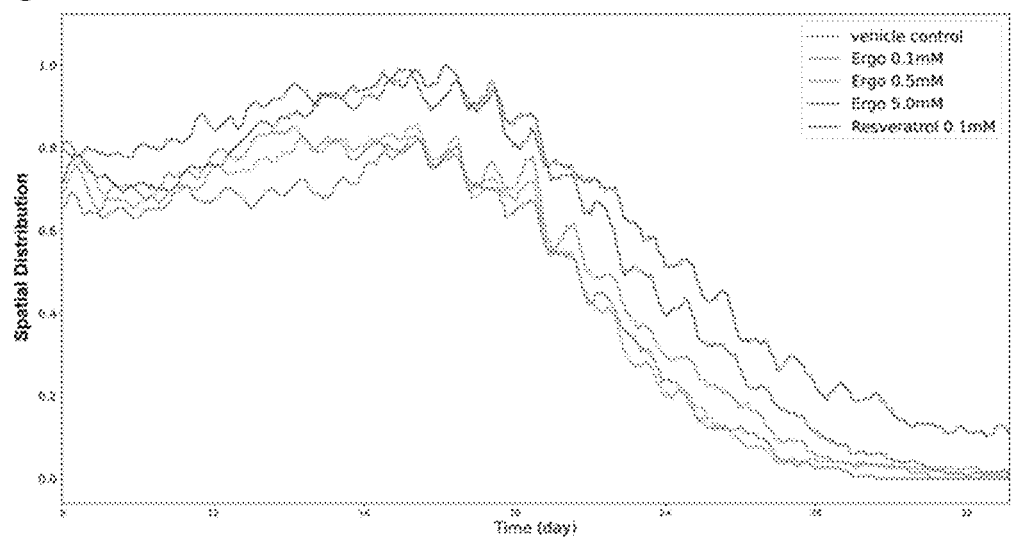
FIGS. 5A-5B show the worm activity (aggregate motility) analysis over duration of lifespan.
Figure 5B:
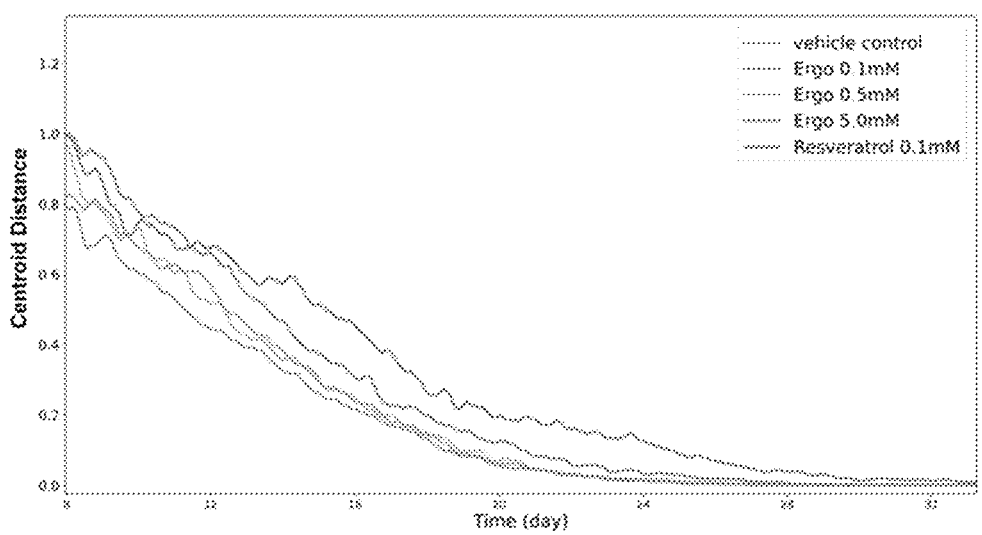

Healthspan Results:

Aggregate Movement. FIGS. 5A-5B show the worm activity (aggregate motility) analysis over duration of lifespan. FIG. 5A is the Spatial Distribution, where "(1-normalized mutual information)" measures changes in the spatial distribution of active worms between time points. FIG. 5B is the Centroid Distance, where the "normalized minimum centroid distance" measures the changes in the location of active worms as a group between time points. Both the Centroid Distance and the Spatial Distribution are concordant with the results and relative ranking of strains in the lifespan analysis. Both the 5 mM Ergothioneine and the Resveratrol groups showed more vigorous movement over the duration of lifespan (FIGS. 5A-5B). The plots are normalized by the number of worms still alive and moving. The Resveratrol plot does not reach zero due to a small number of worms still moving at the end of the experiment.

Figure 6A:
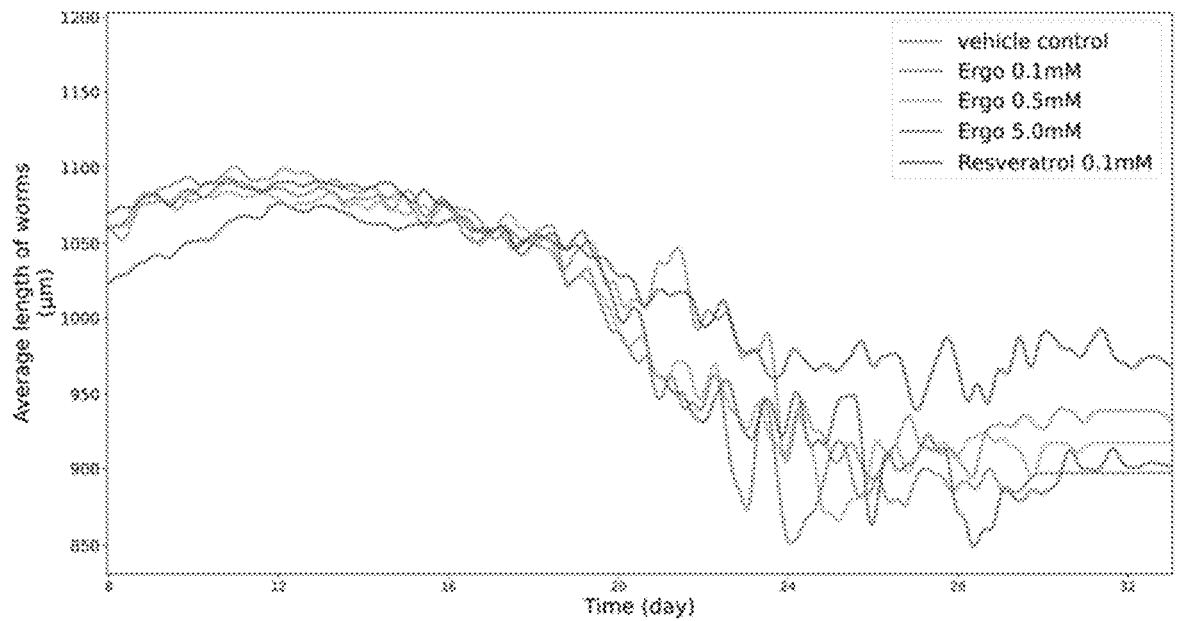
FIGS. 6A-6C are showing morphology analysis over duration of lifespan.
Figure 6B:
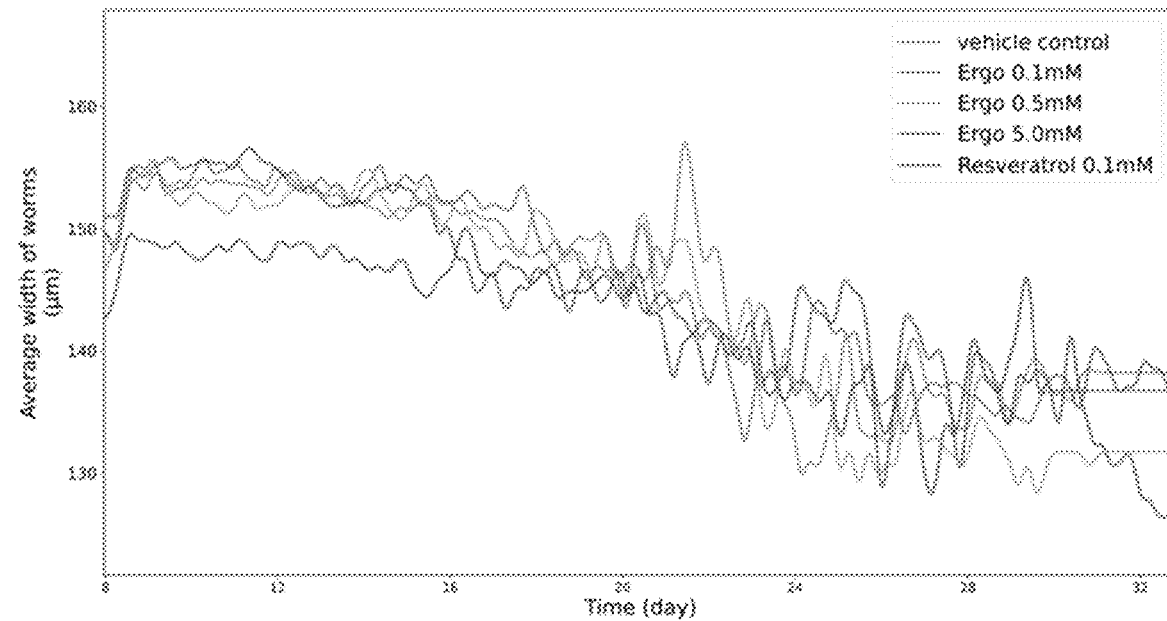
Figure 6C:
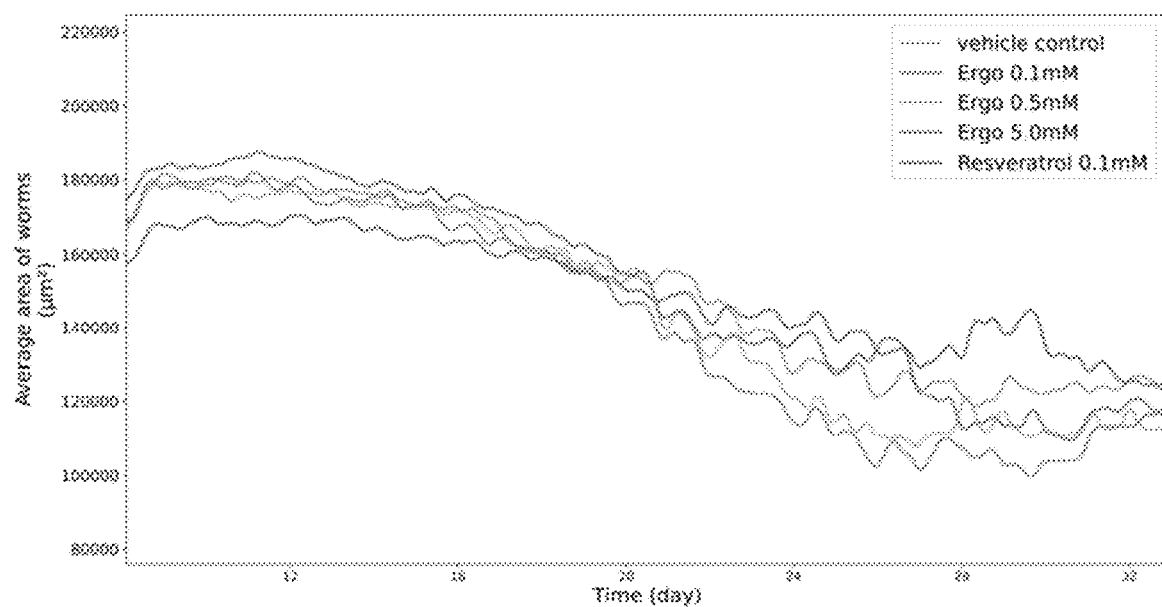

Worm Morphology. FIGS. 6A-6C are showing morphology analysis over duration of lifespan. FIG. 6A shows the average length of worms, which was measured along a central spline fitted to the worm outline. FIG. 6B shows the average width of worms, which was measured at the widest point orthogonal to the central spline. FIG. 6C shows the average area of worms, which is the total pixel area of the worm outline converted to $\mu m^2$. The overall length of worms was consistent with expected worm size and no differences were detected between the three treatments over the course of the lifespan. The Resveratrol treated worms were overall slightly smaller earlier in the assay but remained larger in the late life stages. Treatment with Ergothioneine, however, did not produce detectable changes in morphology despite increasing lifespan at the 5 mM dosage (FIGS. 6A-6C). Sometimes, if a compound is having a strong secondary effect this will appear as a major change in morphology—e.g. induction of dauer (dormancy) results in longer, skinnier worms. Ergothioneine appears to impact longevity without significant direct morphological changes.

Figure 7:
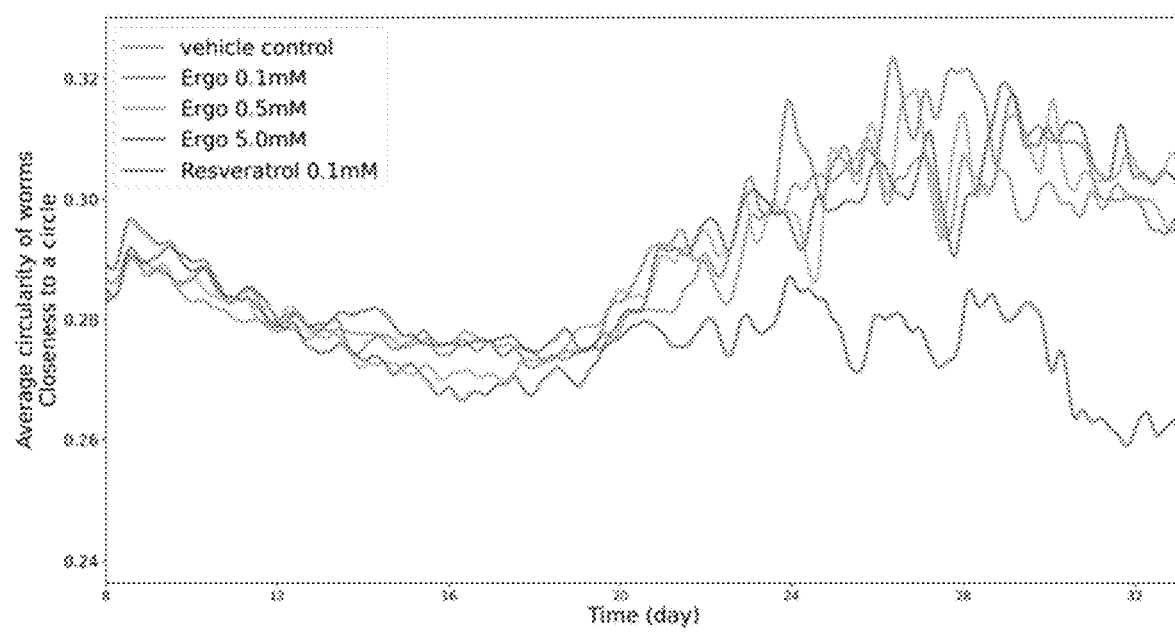
FIG. 7 shows the average circularity of worm, which measures how close the worm's shape and posture is to a perfect circle, with a perfect circle having circularity of 1.

Average Circularity. The Average Circularity Assay indicates worm heath by describing how closely the shape and posture of the worms is enclosed within a circle. Healthy, active worms maintain an elongated, albeit sinusoidal posture. As unhealthy and aged worms lose muscle function, they increasingly adopt a curled, bunched, or folded state in addition to a stout and wrinkled morphology. Hence, the shape of unhealthy worms is more readily enclosed by a perfect circle—their circularity is closer to 1. FIG. 7 shows the average circularity of worm, which measures how close the worm's shape and posture is to a perfect circle, with a perfect circle having circularity of 1.

Worms treated with ergothionene showed only slight differences in their overall circularity peaking at around 16 days (FIG. 7) suggesting that they transitioned into late life in a slightly more healthy and active state. The Resveratrol treated worms, by contrast, maintained a more elongated posture well into late life.

Taken together, the morphology of Ergothioneine-treated worms was not heavily altered relative to control. This provides a good indication that the higher dose of Ergothioneine is able to exert its effects on longevity without inducing starvation or a dauer (dormancy) state. This can happen when a compound causes food aversion or a nutritional deficiency. However, it also does not provide a detectable prolongation of more youthful morphology.

Example 4

This example describes the gene expression pattern in Ergothioneine-treated *C. elegans* worms.

To identify potential mechanisms of action through which Ergothioneine could affect aging, global gene expression was analyzed by mRNA sequencing (RNA-Seq). Both young (adult day 3) and aged (adult day 10) worms were collected from the same population of worms tested in the lifespan assay.

Differential gene expression was performed with EdgeR using false likelihood ratio tests based on fitting linear models. The likelihood ratios were used to determine the p-values which were subsequently corrected for using the BH false discovery rate (fdr) method. Ultimately, differentially expressed genes (DEG) were defined as genes with an fdr-corrected p-value of 0.05 or lower, as well as a change in expression of at least 2-fold in a given between-group comparison. In this study, the comparison groups in Table 5 were used:

TABLE 5

Comparison groups for differential gene expression

| Group | Experiment | Control |
| --- | --- | --- |
| 1 | Ergo SmM day 3 | Vehicle day 3 |
| 2 | Ergo SmM day 10 | Vehicle day 10 |
| 3 | Vehicle day 10 | Vehicle day 3 |
| 4 | Ergo SmM day 10 | Ergo SmM day 3 |

Multidimensional scaling makes it possible to see strong patterns in large, complex data sets by reducing the data to two or three dimensions. When the data is plotted along these few dimensions, the samples form clustered based on their overall similarity to one another. The distance between samples is calculated based on the Biological Coefficient of Variation (BCV).

Volcano plots for each comparison were used to show log fold change of gene expression against its p-value of the specified comparison.

Reading Volcano Plots (log 2 fold change, Log FC): Positive values mean that the gene is more expressed in Treatment, and negative values mean the gene is more expressed in Control. The farther the dot is from the origin point on the x-axis, the greater the expression fold-change. Genes represented in green show a larger than 2-fold change in expression but are not deemed statistically significant due to replicate variability or low read count. Genes represented by red dots show greater than 2-fold change and expression that is statistically significant. The higher on the y-axis, the greater the calculated level of significance.

Reading Gene Ontology Enrichment (Pathway) Analysis Tables: Functional characterization of gene lists using Gene Ontology (GO) enrichment analysis is a common approach in transcriptomic analysis. Once the table of differentially expressed genes has been created, the annotation of those genes by biological process (BP), molecular function (MF), or cellular compartment (CC), is cataloged and a comparison is made between the likelihood of seeing genes in that category (ontology) being enriched in the list of differentially-expressed genes when compared to a random selection of genes. This allows patterns due to the interactions of multiple genes to emerge.

Dimensional Analysis

Figure 8:
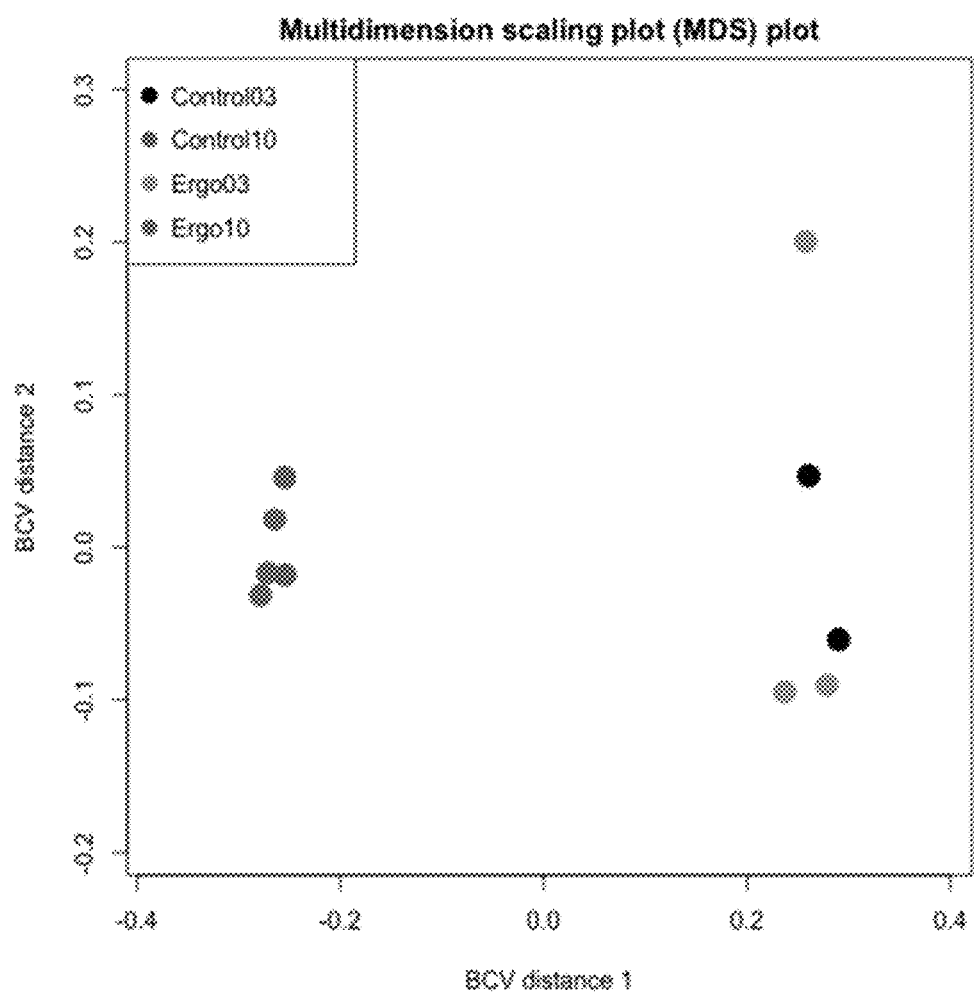
FIG. 8 is a multidimension scaling plot (MDS) that shows multidimensional scaling to embed expression of all included genes into a 2-dimensional plot.

FIG. 8 is a multidimension scaling plot (MDS) and shows multidimensional scaling to embed expression of all included genes into a 2-dimensional plot. BCV=Biological coefficient of variance. Black=control day 3, Red=control day 10, green=Ergo day 3, blue=Ergo day 10. Dimensional reduction of the data to a 2-dimensional plot shows the replicates for each condition in six distinct, non-overlapping clusters. This indicates that each condition holistically exhibited a distinct and reproducible expression profile (FIG. 8). The relative positions of each condition on the plot also agrees with the expected results. All of the Day 3 treatments (black, green) are horizontally separated from all of the Day 10 treatments (blue, red) but vertically aligned with each other, as are the Day 10 treatments (FIG. 8). X-axis components, therefore, represent differences between young and aged worms regardless of treatment. The Day 3 replicates were more vertically spread whereas there was little if any separation between the Day 10 replicates, indicating a stronger impact of treatment at the Day 3 time point. The lack of separated clusters between the treated and untreated samples indicates that differences are more likely to arise in individual key genes rather than global changes in gene expression.

Differential Gene Expression

Figure 9A:
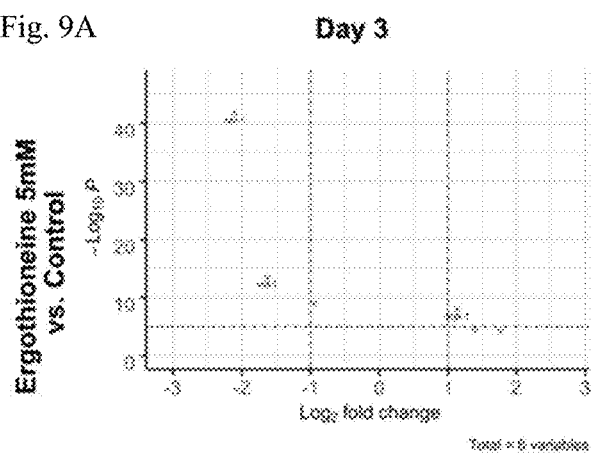
FIGS. 9A-9D are the volcano plots for all three comparison groups. Red dots indicate differential gene expression that exceeds defined significance and fold-change thresholds.
Figure 9B:
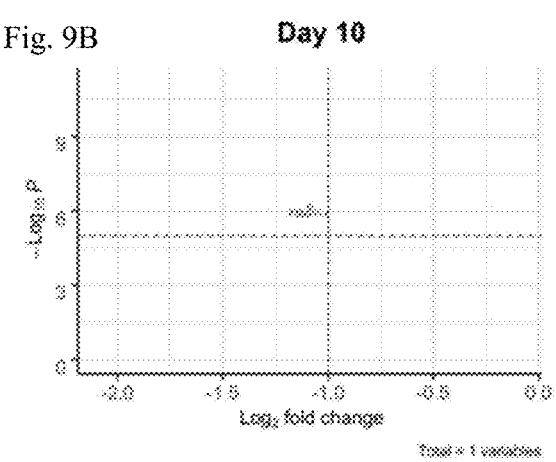
Figure 9C:
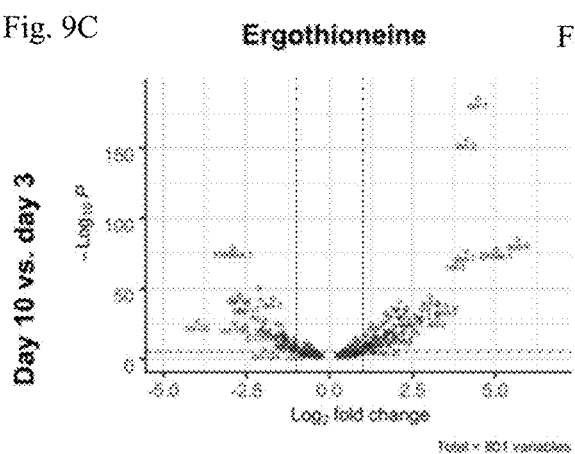
Figure 9D:
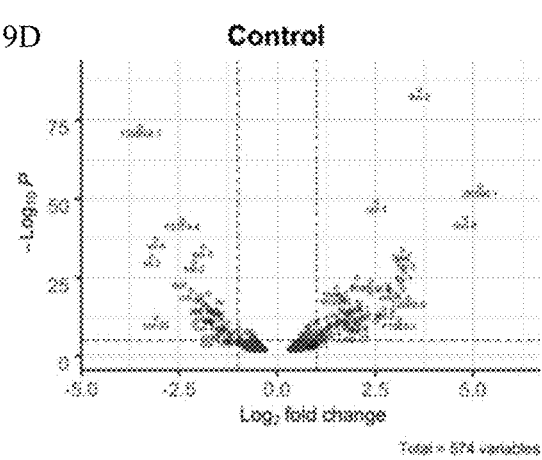

To identify genes that are differentially expressed upon treatment with Ergothioneine, the gene counts for each of the Ergothioneine-treated samples were compared against the control. FIGS. 9A-9D are the volcano plots for all three comparison groups. Red dots indicate differential gene expression that exceeds defined significance and fold-change thresholds. FIG. 9A, Ergothioneine Day 3 vs. Control Day 3. FIG. 9B, Ergothioneine Day 10 vs. Control Day 10. FIG. 9C, Ergothioneine Day 10 vs. Ergothioneine Day 3. FIG. 9D, Control Day 10 vs. Control Day 3. Gray dots=not significant, green=>2-fold change in expression, blue=P-value<0.05, red=2-fold change in expression and P-value<0.05. The volcano plots in FIGS. 9A-9D show the distribution of genes for each condition with a P-value 2.0. Ergothioneine treatment produced only 3 genes differentially expressed above threshold at Day 3: cpr-1, mtl-1, argk-1. However, each of these genes has been previously implicated in worm longevity and will be discussed below. Only 1 gene was differentially expressed above threshold at Day 10. This gene F55G11.4 is uncharacterized in *C. elegans* and does not have a clear ortholog in humans or other animal models.

Figure 10:
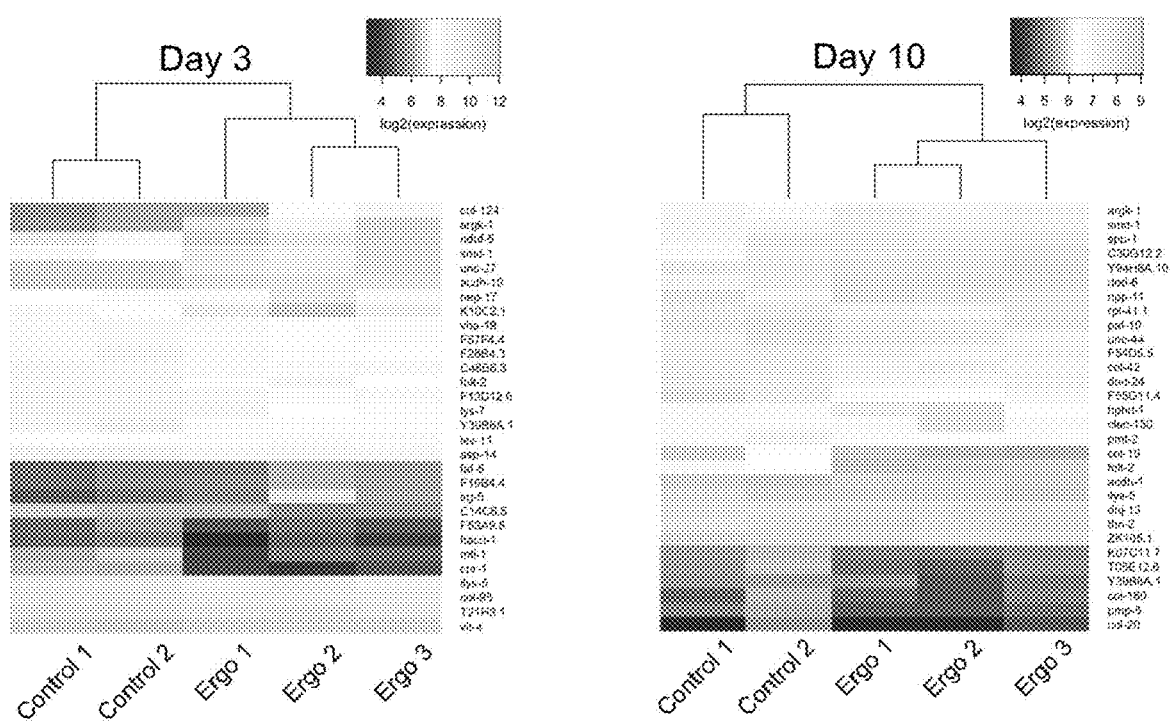
FIG. 10 are heatmaps showing the top thirty differentially expressed genes for each condition. Left panel is from young day 3 worms and right panel is from aged day 10 worms.

Expanding to the top 30 DEG, the replicates cluster within their own treatment are shown in FIG. 10, which are heatmaps showing the top thirty differentially expressed genes for each condition. Left panel is from young day 3 worms and right panel is from aged day 10 worms. In both panels, the left two columns are controls and the right three columns are samples treated with Ergothioneine at 5 mM. Heatmap columns represent individual biological replicates. Colormap indicates log 2 (expression in CPM). FIG. 10 shows that the response was consistent within and between groups. Although most do not surpass the stringent significance cutoff shown in the volcano plots (see FIGS. 9A-9D), there are several relevant genes within the top DEG that have been associated with either worm longevity, stress response, or response to xenobiotic compounds (FIG. 10, Table 6, Table 7). Table 6 shows the top 20 differentially expressed genes under Ergothioneine treatment at Day 3 ranked by P-value. Table 7 shows the top 20 differentially expressed genes under Ergothioneine treatment at Day 10.

TABLE 6

Ergothioneine 5 mM vs. Vehicle Control: Top differentially expressed genes at Day 3. Gene function annotations collected from WormBase are shown.

| gene | Log FC | PValue | Protein product | Function description |
|---|---|---|---|---|
| cpr-1 | −2.10 | 1.67E−42 | Cysteine PRotease related | Cysteine protease of the cathepsin B-like cysteine protease family; |
| mtl-1 | −1.63 | 3.94E−14 | MeTallothionein | MTL-1 functions in metal detoxification and homeostasis and in stress adaptation. mtl-1 is upregulated by DAF-16 in daf-2 mutants. |
| Y3986A.1 | −0.95 | 1.04E−09 | not known | |
| argk-1 | 1.14 | 1.0SE−08 | ARGinine Kinase | Is predicted to enable ATPbinding activity; arginine kinase activity; and creatine kinase activity. Is an ortholog of human CKMT2 (creatine kinase, mitochondrial 2). |
| irg-5 | 1.39 | 3.47E−05 | Infection Response Gene | Is involved in defense response to Gram-positive bacterium. |
| col-124 | 1.76 | 6.18E−05 | COLlagen | Structural constituent of cuticle. |
| hacd-1 | −1.06 | 4.28E−04 | Hydroxy-Acyl-CoA Dehydrogenase | Is predicted to enable NAD+ binding activity and oxidoreductase activity |
| folt-2 | −0.54 | 5.93E−04 | FOLate Transporter family | FOLT-2 is orthologous to the human folate transporters. |
| F28B4.3 | −0.48 | 1.15E−03 | not known | Is affected by several genes including daf-16; daf-2; and skn-1 based on microarray; proteomic; and RNA-seq studies. |
| lys-7 | −0.70 | 1.19E−03 | LYSozyme | Encodes an enzyme homologous to an antimicrobial lysozyme |
| vit-4 | −0.64 | 1.27E−03 | VITellogenin structural genes (yolk protein genes) | Is predicted to enable lipid transporter activity and nutrient reservoir activity. |
| ctsa-1.2 | −0.48 | 2.54E−03 | CaThepSin A homolog | |
| F57F4.4 | −0.43 | 3.46E−03 | not known | Located in membrane raft. |
| col-95 | −0.56 | 3.74E−03 | COLlagen | col-95 encodes a collagen. |
| Hys-5 | −0.57 | 3.93E−03 | Invertebrate LYSozyme | Is predicted to enable lysozyme activity. |
| F53A9.8 | −0.73 | 4.83E−03 | not known | Involved in defense response to Gram-positive bacterium. |
| C14C6.5 | −0.59 | 4.95E−03 | not known | Involved in the transcriptional, innate immune response towards several different bacterial pathogens. |
| smd-1 | −0.35 | 8.29E−03 | SAM Decarboxylase | SMD-1 functions in polyamine biosynthesis |
| F16B4.4 | 0.66 | 8.37E−03 | not known | Is expressed in hypodermis. |
| ctsa-2 | −0.50 | 9.68E−03 | CaThepSin A homolog | Predicted to enable serine-type carboxypeptidase activity. Located in membrane raft. |

TABLE 7

Ergothioneine 5 mM vs. Vehicle Control: Top differentially expressed genes at Day 10. Gene function annotations collected from WormBase are shown.

| gene | Log FC | P Value | Protein product | Function description |
|---|---|---|---|---|
| F55G11.4 | −1.09 | 6.55E−07 | not known | Encodes a protein containing a CUB-like domain conserved amongst nematodes; Expression is increased in response to bacterial infection, suggesting a role in the defense response. |
| folt-2 | −0.49 | 2.32E−03 | FOLate Transporter family | Encodes a putative folate transporter, FOLT-2 is orthologous to the human folate transporters SLC19A1, SLC19A2, and SLC19A3 |
| T05E12.6 | −0.62 | 5.36E−03 | not known | |
| dod-6 | 0.69 | 9.36E−03 | Downstream Of DAF-16 (regulated by DAF-16) | Involved in pharyngeal gland morphogenesis. |
| pmp-5 | −0.64 | 1.39E−02 | Peroxisomal Membrane Protein related | Predicted to enable ATP binding activity and ATPase-coupled transmembrane transporter activity. Ortholog of human ABCD4 |
| col-19 | −0.47 | 1.91E−02 | COLiagen | Member of the collagen superfamily containing collagen triple helix repeats. |
| Y3986A.1 | −0.38 | 2.08E−O2 | not known | |
| pmt-2 | −0.38 | 2.19E−02 | Phosphoethanolamine MethylTransferase | Encodes an experimentally validated N-methyltransferase re9uired for phosphocholine biosynthesis and viability; lacks known mammalian orthologs, but has orthologs in parasitic nematodes, fish, amphibians, echinoderms, plants, alveolata, and bacteria |
| C30G12.2 | 0.55 | 3.07E−02 | not known | |
| dod-24 | −0.49 | 3.16E−02 | Downstream Of DAF-16 (regulated by DAF-16) | Involved in defense response to Gram-negative bacterium. |
| thn-2 | 0.31 | 3.85E−02 | THaumatiN family | Is involved in defense response to Gram-negative bacterium and defense response to Gram-positive bacterium. |
| Y94H6A.10 | 0.43 | 4.92E−02 | not known | |
| smd-1 | 0.26 | 5.19E−02 | SAM Decarboxylase | smd-1 encodes an S-adenosylmethionine decarboxylase; SMD-1 functions in polyamine biosynthesis |
| K07C11.7 | −0.43 | 5.73E−02 | not known | Encodes one of three C. elegans metallophoshopesterase that are related to human 239FB associated with various tumors and WAGR syndrome. |
| dec-150 | −0.45 | 5.98E−02 | C-type LECtin | Predicted to enable carbohydrate binding activity. |
| dnj-1 3 | 0.26 | 6.00E−02 | DNaJ domain | Encodes a protein containing a DnaJ ('J') domain (prokaryotic heat shock protein). |
| argk-1 | 0.36 | 6.31 E−02 | ARGinine Kinase | Is predicted to enable ATP binding activity; arginine kinase activity; and creatine kinase activity. |
| ilys-5 | 0.36 | 7.35E−02 | Invertebrate LYSozyme | Predicted to enable lysozyme activity. |
| col-20 | −0.64 | 7.82E−02 | COLlagen | Encodes a collagen |
| col-42 | −0.29 | 8.51E−02 | COLlagen | Predicted to be a structural constituent of cuticle. |

50

Gene Ontology (GO) Enrichment

In all of the Ergothioneine-treated groups the GO term enrichment for each process was only represented by a single gene despite exceeding a significance cutoff (see the Up/Down column in Tables 8 and 9).

TABLE 8

Top over-represented GO terms Ergothioneine 5 mM vs control day 3.

| GO ID | Term | Ont. | N | Up | Down | P value |
|---|---|---|---|---|---|---|
| GO:0042302 | structural constituent of cuticle | MF | 17 | 1 | 0 | 0.02 |
| GO:0005581 | collagen trimer | CC | 18 | 1 | 0 | 0.02 |
| GO:0050830 | defense response to Gram-positive bacterium | BP | 22 | 1 | 0 | 0.02 |
| GO:0042742 | defense response to bacterium | BP | 43 | 1 | 0 | 0.04 |
| GO:0009617 | response to bacterium | BP | 43 | 1 | 0 | 0.04 |

TABLE 8-continued

Top over-represented GO terms Ergothioneine 5 mM vs control day 3.

| GO ID | Term | Ont. | N | Up | Down | P value |
|---|---|---|---|---|---|---|
| GO:0006955 | immune response | BP | 44 | 1 | 0 | 0.05 |
| GO:0045087 | innate immune response | BP | 44 | 1 | 0 | 0.05 |
| GO:0002376 | immune system process | BP | 45 | 1 | 0 | 0.05 |

GO ID: Unique GO ID# cataloged at geneontology.org.
Ont: Ontology class biological process (BP), molecular function (MF), cellular compartment (CC).
N: Total number of Genes classified in that GO term.
Up/Down: The number of genes in that GO term (out of N) that are up or down-regulated.
P-value: Significance of gene enrichment (up) or depletion (down) in the set of differentially expressed genes vs. the null set.

TABLE 9

Top under-represented GO terms Ergothioneine 5 mM vs control day 3.

| GO ID | Term | Ont | N | Up | Down | P value |
|---|---|---|---|---|---|---|
| GO:0046870 | cadmium ion binding | MF | 1 | 0 | 1 | 0.00 |
| GO:0010288 | response to lead ion | BP | 1 | 0 | 1 | 0.00 |
| GO:0046689 | response to mercury ion | BP | 1 | 0 | 1 | 0.00 |
| GO:0046686 | response to cadmium ion | BP | 4 | 0 | 1 | 0.00 |
| GO:0005507 | copper ion binding | MF | 6 | 0 | 1 | 0.01 |
| GO:0004197 | cysteine-type endopeptidase activity | MF | 17 | 0 | 1 | 0.02 |
| GO:0010038 | response to metal ion | BP | 17 | 0 | 1 | 0.02 |
| GO:0009408 | response to heat | BP | 28 | 0 | 1 | 0.03 |
| GO:0010035 | response to inorganic substance | BP | 28 | 0 | 1 | 0.03 |
| GO:0005764 | lysosome | CC | 31 | 0 | 1 | 0.03 |
| GO:0000323 | lytic vacuole | CC | 32 | 0 | 1 | 0.03 |
| GO:0009266 | response to temperature stimulus | BP | 33 | 0 | 1 | 0.03 |
| GO:0005615 | extracellular space | CC | 35 | 0 | 1 | 0.04 |
| GO:0008234 | cysteine-type peptidase activity | MF | 36 | 0 | 1 | 0.04 |

GO terms under-represented in Ergothioneine-treated worms at day 3.
GO ID: Unique GO ID# cataloged at geneontology.org.
Ont: Ontology class biological process (BP), molecular function (MF), cellular compartment (CC).
N: Total number of Genes classified in that GO term.
Up/Down: The number of genes in that GO term (out of N) that are up or down-regulated. Range is shown for all conditions.
P-value: Significance of gene enrichment (up) or depletion (down) in the set of differentially expressed genes vs. the null set.

The GO enrichment tables are shown here for illustration and to highlight ontology represented among the DEG. Multiple processes are likely represented by the same single gene. As GO enrichment analysis would not be strongly informative for this specific data set, analysis will focus on the individual genes and the longevity pathways represented in the Mechanism of Action report below.

Example 5

This example describes identification of cellular pathways that are most likely modulated by treatment with Ergothioneine. To accomplish this, the genes differentially expressed after Ergothioneine treatment were first mapped to core established longevity pathways from the literature. Then the mapping was expanded to intersecting and supporting pathways. This placed the transcriptomic data within the context of well-characterized biological pathways, particularly several related to longevity.

Longevity-Focused Pathway Analysis

Differentially expressed genes (DEGs) were mapped to known physiological pathways and then examined for coherent linkages between pathways related to longevity. These pathways were drawn from WormBase, KEGG, and other published databases and literature. For each condition, the DEGs were filtered on a more relaxed P value cutoff than the initial differential gene expression to capture broad evidence for a pathway from many small changes as opposed to highly significant individual genes of interest. For visualization, pathway genes were given a score based on the fold change weighted by the log of the P value, and this score was color mapped by magnitude and direction to produce the pathway diagram in FIG. 11.

Figure 11:
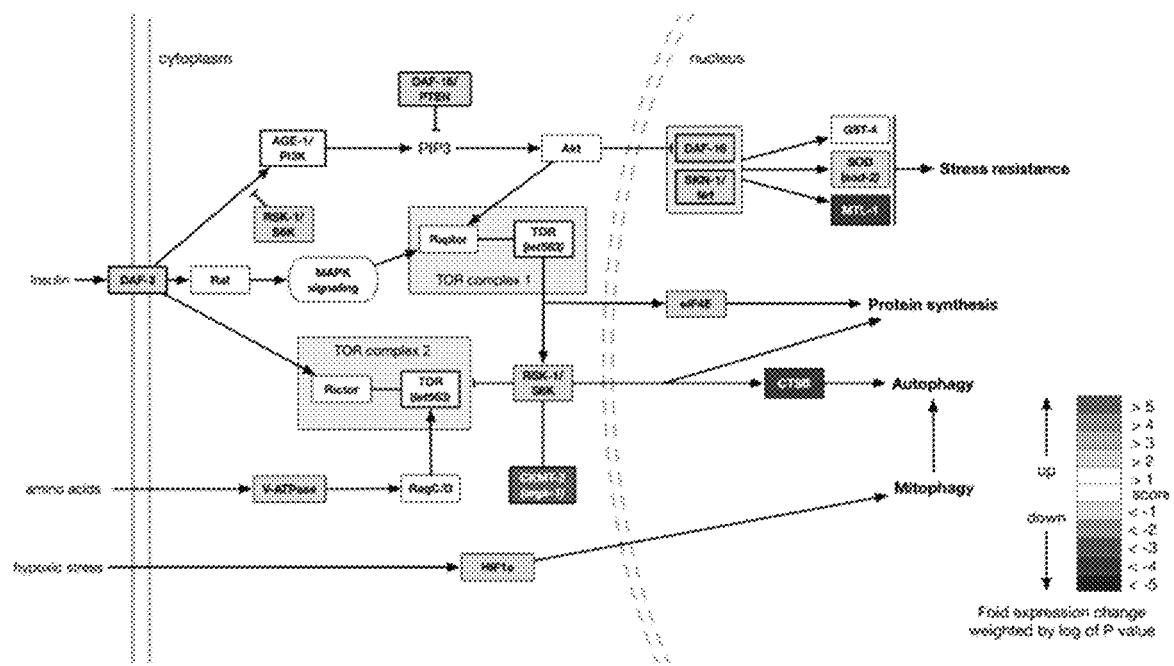
FIG. 11 is diagram showing a summary of pathway mapping to recognized aging-related pathways for Ergothioneine treatment.

FIG. 11 is a summary of pathway mapping to recognized aging-related pathways for Ergothioneine treatment. Colored score increments indicate degree of up-(red) or down-(blue) regulation weighted by the log of the P value such that each increment approximates one inverse log of P value. Uncolored objects indicate components that were not detected in the data. Top red indicates P value<0.0001 and so on. Solid lines indicate direct pathway connections and dashed lines indicate indirect or multi-step connections. Where lists of differentially expressed genes have been condensed into a module, the number of genes is indicated.

Starting with the canonical longevity pathways, the intersections with supporting pathways was then examined to expand the pool of evidence of whether a pathway is impacted by the treatment. Although only a few of the genes might individually have highly significant changes in expression, collectively, the connectivity of the pathways can suggest a coherent hypothesis for a mechanism of action. Since a gene or pathway might be upregulated in response to a stress or downregulated due to relief of the stress, direction of change is not considered, only whether the expression of the genes has changed is considered.

Worms treated with Ergothioneine showed changes in expression of genes involved with insulin response and energy metabolism, including several key members of canonical longevity pathways (FIG. 11). This included changes in expression of daf-2 (Insulin receptor), daf-16, daf-18 (PTEN), three key components of the insulin signaling pathway. One major target of this pathway, mtl-1, was strongly downregulated; several component genes involved in autophagy, as well as genes involved with protein translation, ife-2 (eIF4E) (FIG. 11) were also downregulated. There were some changes mapped to other longevity pathways such as mitochondrial health, autophagy, and oxidative stress response, but these were less extensive. How these pathways might contribute to longevity within the context of the Ergothioneine gene expression data is summarized below.

Insulin Signaling (daf-2, daf-18, rsks-1)

The insulin/insulin-like growth factor-1 signaling (IIS) pathway was the first pathway implicated in genetic regulation of lifespan and aging. The IIS signaling pathway regulates longevity through three key components: the worm insulin receptor DAF-2, the kinase AGE-1, and the transcription factor DAF-16. As shown in FIG. 11, Ergothioneine treatment modulated the expression of several genes linked to this pathway. The discovery that loss of function of the worm insulin receptor DAF-2 could more than double lifespan in C. elegans was a landmark finding that helped launch the field of aging research. In response to Ergothioneine treatment, daf-2 and three other key pathway components were slightly downregulated. Both daf-18, which encodes the ortholog of human Phosphatase and Tensin (PTEN), and rsks-1, which encodes Ribosomal Protein S6 Kinase, regulate the activity of the Phosphatidylinositol 3-Kinase, AGE-1, which transduces the insulin response signal. The transcriptional output of this pathway is carried out by the transcription factor DAF-16, which controls expression of a large number of genes (Murphy, Coleen T., Steven A. McCarroll, Cornelia I. Bargmann, Andrew Fraser, Ravi S. Kamath, Julie Ahringer, Hao Li, and Cynthia Kenyon. 2003. "Genes That Act Downstream of DAF-16 to Influence the Lifespan of *Caenorhabditis Elegans*." Nature 424 (6946): 277-83). In addition to a slight downregulation of daf-16 itself, several targets of DAF-16 regulation involved in longevity and stress response, including mtl-1 and sod-2, were also downregulated. Their contributions are described below.

Autophagy

Autophagy is a cellular process that catabolizes cellular components to maintain energy homeostasis and protect against stress. Activation of autophagy is associated with increased longevity (Hansen, Malene, David C. Rubinsztein, and David W. Walker. 2018. "Autophagy as a Promoter of Longevity: Insights from Model Organisms." Nature Reviews. Molecular Cell Biology 19 (9): 579-93). The gene cpr-1, which encodes a worm ortholog of Cathepsin B, was significantly downregulated in Ergothioneine-treated worms. Cathepsins control proteolytic degradation within the lysosome. A subset of autophagy, mitophagy promotes longevity through the turnover of declining mitochondria. In addition to cpr-1, several other genes involved with autophagy had less significant changes in expression.

mTOR Signaling and Energy Metabolism (Daf-15, Rict-1, Let-363, Rsks-1)

mTOR is a key nutrient sensor and master regulator of growth and energy metabolism in animals. Signaling through mTOR involves two distinct protein complexes, mTORC1 and mTORC2 that regulate different physiological processes. Although TOR signaling pathways share many components and interact with the IIS pathway, in this case no evidence indicated substantial direct modulation of the TOR pathway.

Mitochondrial Health and Oxidative Stress (Sod-2, Oxidative Phosphorylation Genes)

Mitochondria provide essential energy for the cell. This organelle is also a major source of reactive oxygen species (ROS) that causes oxidative stress and damage to proteins. Disruptions in mitochondria function, particularly in electron transport exacerbates overproduction of ROS. Conditions that promote mitochondrial maintenance and/or turnover (mitophagy) have been linked to extended lifespan and improved health. All animals treated with Ergo showed a slightly decreased expression of superoxide dismutase (SOD-2), a key antioxidant enzyme that breaks down reactive oxygen species. Modulation of several genes involved in oxidative phosphorylation by Ergo treatment can also be an indicator of mitochondrial health and maintenance.

Stress Response (mtl-1, skn-1, sod-2)

With compound treatments such as Ergothioneine, it is common to see expression of many genes involved in response to xenobiotic compounds and innate immune responses that might be responding directly to the drug test compound itself. However, there was also differential expression of key stress response genes linked to longevity: skn-1, mtl-1, sod-2. The transcription factor SKN-1 is an ortholog of human Nuclear Respiratory Factor (Nrf) that works in conjunction with DAF-16 to activate transcriptional responses to xenobiotic and oxidative stress. Several life-extending interventions, such as dietary restriction, involve SKN-1 activation. The slight downregulation of both daf-16 and skn-1 as well as upstream pathway components is consistent with the significant strong downregulation of mtl-1.

Protein Translation (ife-2)

Regulation of protein translation in somatic tissues has also been implicated in longevity. The eukaryotic initiation factor 4E (eIF4E) is encoded by the C. elegans gene ife-2. Although there is a connection between TOR signaling and eIF4E activity, knockdown of ife-2 in C. elegans can extend lifespan independently of both IIS and TOR signaling, suggesting a possible distinct pathway of life extension.

Summary of Differential Gene Expression Analysis

Analysis of differential gene expression produced a relatively small list of significant DEG, yet it is enriched with candidates that have previously been directly implicated in modulating lifespan in C. elegans. Three genes in particular, cpr-1, mtl-1, and argk-1, have been previously shown to directly impact lifespan when their normal expression is perturbed. Multidimensional scaling (MDS) analysis indicated few global differences between Ergothioneine-treated and control worms. Large global differences in gene expression between day 10 and day 3 within each treatment were observed, which is expected. Whereas with some compounds the life extension is coupled with a strong xenobiotic and innate immune response, this response is qualitatively milder with Ergothioneine treatment. Expanding the analysis beyond the first layer of significant DEGs indicated that several key components of the IIS signaling pathway were all slightly downregulated, suggesting a response to Ergo resembling caloric restriction.

What is claimed is:

1. A method for extending lifespan or improving healthspan of a mammal in need thereof, comprising administration to the mammal of a composition comprising a therapeutically effective amount of ergothioneine, or a pharmaceutically acceptable salt, wherein the composition extending lifespan or improving healthspan is by regulation of autophagy, wherein regulation of autophagy comprises downregulating cpr-1 gene expression.

2. The method of claim 1, wherein the mammal is a human, horse, cattle or other ruminants, pig, or a pet.

3. The method of claim 1, wherein the composition is in a form of food, drink, nutritional composition, or pharmaceutical composition.

4. The method of claim 1, wherein the composition is in a form of solution, liquid suspension, parenteral solution, injectable solution, tablet, pill, granule, powder, film, (micro)capsule, aerosol, tonic, syrup, beverage, or dietary supplement.

5. The method of claim 1, wherein the administration is at least once a day or more times a day.

6. The method of claim 1, wherein the administration is via oral, intravenous injectable, intramuscular injectable, intraperitoneal, intranasal, rectal, or sublingual route.

7. The method of claim 1, wherein the administration of the composition is by oral with a daily dose of ergothioneine in the range of 2-2000 mg.

8. The method of claim 7, wherein the daily dose is administered in divided doses or a single dose.

9. The method of claim 1, wherein ergothioneine is a salt.

* * * * *